US009277977B2

(12) United States Patent
Lorch

(10) Patent No.: US 9,277,977 B2
(45) Date of Patent: *Mar. 8, 2016

(54) DENTAL FLOSS

(71) Applicant: Leonard G. Lorch, San Rafael, CA (US)

(72) Inventor: Leonard G. Lorch, San Rafael, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/298,164

(22) Filed: Jun. 6, 2014

(65) Prior Publication Data

US 2014/0283871 A1 Sep. 25, 2014

Related U.S. Application Data

(63) Continuation-in-part of application No. 14/273,338, filed on May 8, 2014, which is a continuation-in-part of application No. 13/348,275, filed on Jan. 11, 2012, now abandoned, which is a continuation-in-part of application No. 13/012,105, filed on Jan. 24, 2011, now Pat. No. 8,381,742, and a continuation of application No. 13/182,349, filed on Jul. 13, 2011, now abandoned.

(51) Int. Cl.
*A61C 15/00* (2006.01)
*A61C 15/04* (2006.01)

(52) U.S. Cl.
CPC ............... *A61C 15/046* (2013.01); *A61C 15/00* (2013.01); *A61C 15/04* (2013.01)

(58) Field of Classification Search
USPC .................................................. 132/323–329
See application file for complete search history.

(56) References Cited

U.S. PATENT DOCUMENTS 1,929,906 A  10/1933  Skokowski 2,029,260 A  1/1936  Eustis et al.
2,142,194 A  1/1939  Karfoil
2,162,240 A  6/1939  Boldusoff
2,646,622 A  7/1953  Christie et al.
2,703,083 A  3/1955  Gross
2,794,479 A  6/1957  Ganz
2,823,672 A  2/1958  Schladermundt et al.
2,862,846 A  12/1958  Blackford et al.
3,754,332 A  8/1973  Warren (Continued)

FOREIGN PATENT DOCUMENTS

WO  WO/2010/040714  4/2010

OTHER PUBLICATIONS

U.S. Appl. No. 13/012,105, Lorch.
3M, Technical Information Sheet Product No. 1538 3M Medical Rayon Woven Tape, Effective Feb. 2007, (c) 2007, 2007, 3M, St. Paul, USA.
3M, Preliminary Technical Information Sheet Product No. 1524 3M Medical Transfer Adhesive, Effective Jun. 2009, (c) 2009, 2009, 3M, St. Paul, USA.

(Continued)

*Primary Examiner* — Robyn Doan
(74) *Attorney, Agent, or Firm* — Donn K. Harms

(57) ABSTRACT

A dental floss apparatus for cleaning the gaps between adjacent teeth which is comprised of a pair of handles that are configured for engagement with the fingers and having one or a plurality of strands of flossing substrate extending therebetween. The floss extends within an opening formed between the ends of the two handles, during tensioned employment of the handles by a user. A dissolvable component may be positioned within the opening through an engagement with one or both of the handles or the flossing substrate. The dissolvable component dissolves to a solution during use to deposit a residue on the surface of the teeth. The solution from the dissolving component may be colorized or fluorescent, and have an additive material such as mouthwash, breath freshener, cooling agent, or flavor.

17 Claims, 30 Drawing Sheets

(56) References Cited

U.S. PATENT DOCUMENTS

| | | | |
|---|---|---|---|
| 3,802,445 A | 4/1974 | Wesley | |
| 3,860,013 A | 1/1975 | Czapor | |
| 3,869,555 A | 3/1975 | Heonis | |
| 4,016,892 A | 4/1977 | Chodorow | |
| 4,162,687 A | 7/1979 | Lorch | |
| 4,270,556 A | 6/1981 | McAllister | |
| 4,315,516 A | 2/1982 | Zappel | |
| 4,315,517 A | 2/1982 | Krag | |
| 4,519,408 A * | 5/1985 | Charatan | 132/321 |
| 4,550,741 A | 11/1985 | Krag | |
| 4,579,221 A * | 4/1986 | Corella | 206/63.3 |
| 4,712,572 A * | 12/1987 | Hovel, III | 132/321 |
| 4,776,358 A | 10/1988 | Lorch | |
| 4,807,752 A | 2/1989 | Chodorow | |
| 4,852,728 A * | 8/1989 | Court | 206/63.5 |
| 4,986,289 A * | 1/1991 | McWhorter | 132/323 |
| 5,033,488 A | 7/1991 | Curtis et al. | |
| 5,057,357 A | 10/1991 | Winebarger | |
| 5,174,314 A * | 12/1992 | Charatan | 132/328 |
| 5,209,251 A | 5/1993 | Curtis et al. | |
| 5,220,932 A | 6/1993 | Blass | |
| 5,226,435 A | 7/1993 | Suhonen et al. | |
| 5,317,070 A | 5/1994 | Brant et al. | |
| 5,357,990 A | 10/1994 | Suhonen et al. | |
| 5,407,623 A | 4/1995 | Zachariades et al. | |
| 5,431,986 A | 7/1995 | Ortega et al. | |
| 5,479,952 A | 1/1996 | Zachariades et al. | |
| 5,518,012 A | 5/1996 | Dolan et al. | |
| 5,566,692 A | 10/1996 | Thornton | |
| 5,657,779 A | 8/1997 | Blass et al. | |
| 5,692,531 A | 12/1997 | Chodorow | |
| 5,794,776 A * | 8/1998 | Corella | 206/388 |
| 5,800,823 A | 9/1998 | Blass | |
| 5,806,539 A | 9/1998 | Blass et al. | |
| 5,819,767 A * | 10/1998 | Dix | A61C 15/043 132/321 |
| 5,819,768 A | 10/1998 | Bible et al. | |
| 5,829,458 A | 11/1998 | Chodorow | |
| 5,897,895 A | 4/1999 | Bongiovanni | |
| 5,911,228 A | 6/1999 | Curtis et al. | |
| 5,911,229 A | 6/1999 | Chodorow | |
| 5,973,290 A | 10/1999 | Noddin | |
| 6,065,479 A | 5/2000 | Chodorow | |
| 6,080,481 A | 6/2000 | Ochs et al. | |
| 6,220,256 B1 | 4/2001 | Dolan et al. | |
| 6,234,182 B1 * | 5/2001 | Berglund | 132/323 |
| 6,539,951 B2 | 4/2003 | Baillie et al. | |
| 6,552,024 B1 | 4/2003 | Chen et al. | |
| 6,596,298 B2 | 7/2003 | Leung et al. | |
| 6,604,534 B2 | 8/2003 | Hill | |
| 6,607,000 B2 | 8/2003 | Marwah et al. | |
| 6,609,527 B2 | 8/2003 | Brown | |
| 6,656,493 B2 | 12/2003 | Dzija et al. | |
| 6,709,526 B1 | 3/2004 | Bailey et al. | |
| 6,740,332 B2 | 5/2004 | Zyck et al. | |
| 7,055,530 B2 | 6/2006 | Husted | |
| 7,175,902 B2 | 2/2007 | Ortega et al. | |
| 7,262,251 B2 | 8/2007 | Kanderski et al. | |
| 7,281,541 B2 | 10/2007 | Lorch | |
| 7,370,658 B2 | 5/2008 | Chodorow et al. | |
| 7,537,450 B2 | 5/2009 | Karazivan | |
| D607,152 S | 12/2009 | Chodorow et al. | |
| 7,632,525 B2 | 12/2009 | Dodds et al. | |
| 7,674,058 B2 | 3/2010 | Berger Sharp et al. | |
| 7,678,397 B2 | 3/2010 | MacQuarrie | |
| 7,736,739 B2 | 6/2010 | Lutz et al. | |
| 7,740,020 B2 | 6/2010 | Lutz et al. | |
| 7,744,922 B2 | 6/2010 | Mane et al. | |
| 7,754,239 B2 | 7/2010 | Mane et al. | |
| 7,807,194 B2 | 10/2010 | Modliszewski et al. | |
| 7,816,341 B2 | 10/2010 | Sewall et al. | |
| 7,819,126 B2 * | 10/2010 | Bush | 132/323 |
| 7,838,590 B2 | 11/2010 | Kanderski | |
| 7,988,997 B2 | 8/2011 | Von Falkenhausen et al. | |
| 8,002,879 B2 | 8/2011 | Hook | |
| 2003/0224090 A1 | 12/2003 | Pearce et al. | |
| 2003/0235630 A1 | 12/2003 | Nussen | |
| 2004/0036193 A1 | 2/2004 | Berry et al. | |
| 2004/0043134 A1 | 3/2004 | Corriveau et al. | |
| 2004/0048231 A1 | 3/2004 | Perlin | |
| 2004/0087467 A1 | 5/2004 | MacQuarrie | |
| 2009/0014025 A1 * | 1/2009 | Lyulyev et al. | 132/324 |
| 2009/0117515 A1 | 5/2009 | Resk | |
| 2009/0120454 A1 | 5/2009 | Ochs et al. | |
| 2009/0120455 A1 | 5/2009 | Ochs et al. | |
| 2009/0142384 A1 | 6/2009 | Muller et al. | |
| 2009/0151747 A1 * | 6/2009 | Bush | 132/324 |
| 2009/0271936 A1 | 11/2009 | Walanski et al. | |
| 2010/0051051 A1 | 3/2010 | Hsu | |
| 2010/0076080 A1 | 3/2010 | Yelm et al. | |
| 2010/0086498 A1 | 4/2010 | Haught et al. | |
| 2010/0124560 A1 | 5/2010 | Hugerth et al. | |
| 2010/0178252 A1 | 7/2010 | Sagel et al. | |
| 2010/0180912 A1 | 7/2010 | Ochs et al. | |
| 2010/0203467 A1 | 8/2010 | Karazivan | |
| 2010/0247586 A1 | 9/2010 | Hugerth et al. | |
| 2010/0249831 A1 | 9/2010 | Vlasblom et al. | |
| 2010/0252063 A1 | 10/2010 | Grossman | |
| 2011/0044916 A1 | 2/2011 | Kohli et al. | |
| 2011/0151737 A1 | 6/2011 | Moore et al. | |
| 2011/0151738 A1 | 6/2011 | Moore et al. | |
| 2011/0233342 A1 | 9/2011 | Marissen et al. | |
| 2011/0239387 A1 | 10/2011 | Hohlbein et al. | |
| 2011/0256509 A1 | 10/2011 | Russell et al. | |
| 2011/0281021 A1 | 11/2011 | Von Falkenhausen et al. | |
| 2013/0081648 A1 | 4/2013 | Dolan et al. | |

OTHER PUBLICATIONS

Bostik, Technical Data Sheet Product Name H20099, Dec. 2009, 2009, Bostik, Wauwatosa, USA.

Bostik, Technical Data Sheet Product Name H2465, Feb. 2009, 2009, Bostik, Wauwatosa, USA.

Bostik, Material Safety Data Sheet Product Name H2465, Jun. 2011, 2011, Bostik, Wauwatosa, USA.

Bostik, Technical Data Sheet Product Name H20099, Feb. 2011, 2011, Bostik, Wauwatosa, USA.

FitesaFiberweb Washougal Inc., FitesaFiberweb Washougal Typical Properties Style 147SXPO090, Sep. 2011, 2011, FitesaFiberweb Washougal, Inc., Washougal, USA.

FitesaFiberweb Washougal Inc., FitesaFiberweb Washougal Typical Properties Style 118SXPO09O, Jun. 2011, 2011, FitesaFiberweb Washougal, Inc., Washougal, USA.

FitesaFiberweb Washougal Inc., FitesaFiberweb Washougal Typical Properties Style 177SLAO09P, Sep. 2011, 2011, FitesaFiberweb Washougal, Inc., Washougal, USA.

Hygenic Corporation, Thera-Band (R.T.M.) Latex Free Exercise Bands, thera-band.com, (c) 2008, thera-band.com/store/products.php?ProductID=28, Hygenic Corporation, Akron, USA.

Leonard G. Lorch, Safeguarded Flossing Device, Quintessence International, Apr. 1981, 415-416, vol. 12, No. 4, Quintessence Publishing Inc., Chicago, USA.

Steven T. Bunn, How to Floss, drbunn.com, (c) 2000-2004 Last updated May 22, 2004, drbunn.com/flossing.htm, Steven T. Bunn, D.D.S., Alexandria, USA.

Leonard Lorch, Instructions on Awesome Floss (R.T.M.) dental floss, Awesome Floss (R.T.M.) dental floss, (c) 2009 Leonard Lorch, Leonard G. Lorch, San Rafael, USA.

Leonard Lorch, How to use Awesome Floss (R.T.M.) dental floss, Awesome Floss (R.T.M.) dental floss, (c) 2010 Leonard Lorch, Leonard G. Lorch, San Rafael, USA.

John A. Dillon, Processing 2D shapes, (c) 2001, May 2001 Industrial Laser Solutions, May 2001, PennWell Corporation, Tulsa, USA.

3M, Product Clinical Data Summary Product No. 1524 3M Medical Transfer Adhesive, Effective Sep. 2010, (c) 2010, 2010, 3M, St. Paul, USA.

3M, Product Clinical Data Summary Product No. 1538 3M Woven Medical Tape, Effective Jan. 1996, 1996, 3M, St. Paul, USA.

\* cited by examiner

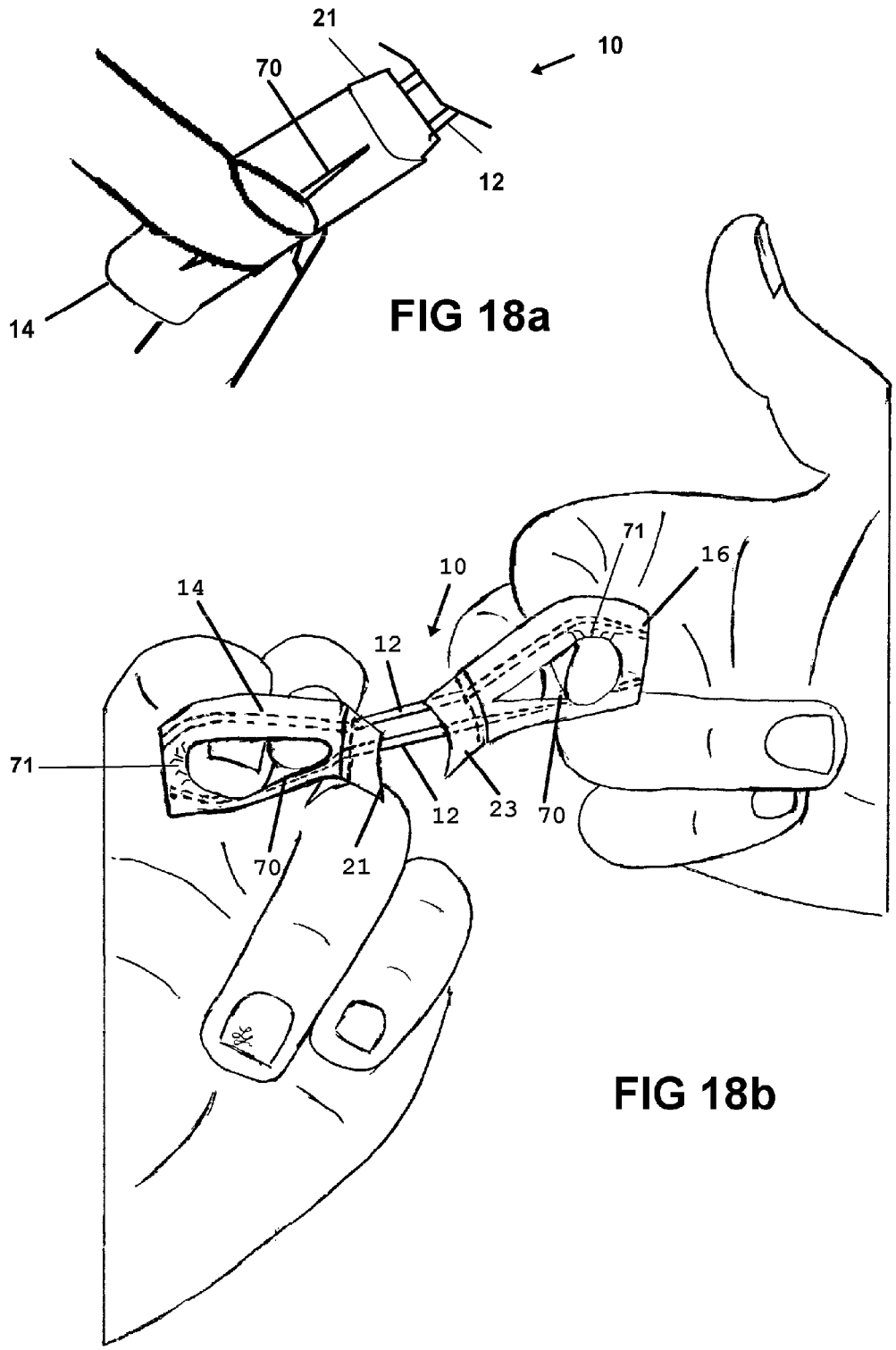

DENTAL FLOSS

This application is a continuation in part from U.S. patent application Ser. No. 14/273,338 filed on May 8, 2014 which is a continuation in part from U.S. patent application Ser. No. 13/348,275 filed on Jan. 11, 2012 which is a Continuation in Part application from U.S. patent application Ser. No. 13/012,105, filed on Jan. 24, 2011, and U.S. patent application Ser. No. 13/182,349, filed on Jul. 13, 2011, which are incorporated by reference herein in their entirety.

BACKGROUND OF THE INVENTION

1. Field of the Invention

The present invention relates to an improved dental flossing apparatus. More particularly it relates to a flossing device and method which provides handles which splay to match the contour of the user's finger rendering the device easier and more comfortable to employ than conventional floss products. The comfort of the splayed finger engagement and a gustatory sensation during use, provide means to induce increased use and thereby encourage regular flossing by the user as part of an ongoing dental hygiene regime.

2. Prior Art

Virtually all dental health practitioners and professionals of the like recommend the use of dental floss for the removal of interdental plaque and particulate from between teeth and under the gum line. These are places that a toothbrush cannot reach and are common initiation sites for tooth decay and gum disease when not cleaned regularly and properly.

Conventional threadlike floss maintains many discouraging aspects to a new or ill-practiced user. It is often difficult to pass the round threadlike floss in between two adjacent teeth due to the resistance encountered by the tooth's side edges. Similarly, children, as well as many adults, find it hard to hold the distal ends of the floss which can painfully 'strangle' the fingers around which they are wrapped during use.

Furthermore, the conventional flossing regimen does not provide any initial or immediate positive reinforcement to the floss trainee other than of course any oral encouragement from an instructor. As a result, there is an inherent tendency of individuals, to reduce their flossing time and possibly halt any and all flossing regimens which the individual may have, with good intentions, initiated. Even in dedicated users having a flossing regimen, such a lack of encouragement or an inducement to continue, can be a resulting cause of reduced flossing over time. Attempts to solve some of these shortcomings and flaws have been attempted as is shown in prior art which include dissolvable components such as substrates and capsules for positive reinforcement.

U.S. Pat. No. 7,281,541 to Lorch, while a definite improvement in the realm of flossing, teaches dental floss comprised of a dissolving component formed of a planar flossing substrate with one or a plurality of apertures formed therein. About each aperture is a pair of edible substrate portions slightly larger than the aperture and joined together through the aperture in the substrate thereby securing it to the latter. In use the edible substrate that is flavored and/or impregnated with medicine, is dissolved or temporarily imparted onto the tooth giving the user a temporary flavor or visual stimulus providing positive reinforcement of the procedure. However, in some individuals, the engagement of the edible substrate dissolving component to the planar substrate may impart a difficulty in the insertion of the floss to translatabley engage in between two adjacent teeth. Surprisingly this is due to the added thickness of the initially blocking, not just dissolving, edible substrate. Further, individuals may find added difficulty in gripping the device similar to the 'strangling' problem associated with conventional floss as mentioned above. As such, there is a continuing and unmet need for an improved device that when employed for flossing, immediately provides an easy and comfortable means to do so, while concurrently freshening breath during flossing and increasing the effectiveness of such a flossing session. The device should be easy to grasp with any of the user's fingers without numerous wraps therearound as is required of floss dispensed from containers. It should provide finger-engageable and ingressible ends to not only assist in positioning the floss in the user's mouth, but also to aid in the user engaging in easy employment of the proper flossing techniques and procedures set forth by a dental professional. Further, the device should provide positive reinforcement such as a perceived health advantage or a gustatory inducement to employ, and continue to use floss in an ongoing manner to users.

SUMMARY OF THE INVENTION

The device herein disclosed and described achieves the above-mentioned goals in surmounting the shortcomings of prior art. In a preferred mode, the device accomplishes this object through the provision of one or a plurality of any conventional commercially available coated, impregnated, waxed or unwaxed flossing substrates extending between two planar grips or handles. In a second, preferred mode of the device, an aperture formed within a planar flossing substrate is provided also with two handles.

The device employs a first and second surface and a first and second end each engaged with a handle. The second end of the device is substantially a mirror of the first end. The flossing substrate extends between and connects the handles at a substantially central location thereon. These handles provide for engagement to the hand through compression between the thumb and one finger or with that finger, thereby eliminating the conventional need to wind the distal end of the flossing substrate about one's finger which frequently results in a strangulation of a user's fingers. The finger-engageable handles are most preferably, a flexible hypoallergenic adhesive cloth tape commercially available as listed product number 1538 as manufactured by the 3M Company or TYVEK nonwoven available from Dupont. The employment of TYVEK nonwoven for the handle formation is especially preferred in that it renders the device entirely recyclable.

However, as those skilled in the art will no doubt realize upon reading this disclosure, the handles may be any woven or nonwoven, non-stretchable or substantially non-stretchable fabric, employing, or imparted with an adhesive backing suited for the intended purpose of the device herein as will become apparent shortly.

In addition, the finger-engageable handles may include a longitudinal slot, slit, or aperture disposed substantially in a mid-portion along the width of the handles of the device. The slot, slit, or aperture communicates through the opposing surfaces of the handles and renders them more easily finger-engageable. This is especially true in that the slit, when the handles are in tensioned engagement between or with fingers and provide a means to form a splay to the substantially flat handles in a curved or three dimensional manner when in the as used mode. This splay formation is especially preferred as it causes a partial wrapping of the material about the curved surface of the user's thumb or a forefinger. This splay, much like the friction enhancing adherent noted herein, provides increased comfort and a significant means for frictional enhancement and resulting increase in the ability of the user to grip and maintain their finger-engagement with the device in the as-used mode.

Additionally, the slit, slot, or aperture provides the user a means to substantially ingress their thumb or a forefinger through the slot for a contact therebetween. This results in an increased ability to the user for gripping and re-orienting of the device as may be desirable for flossing hard to reach places in the mouth.

Due to the tension required for flossing it is particularly preferred that the finger-ingressible slits, slots, or apertures, are formed in material which is partially or substantially non-tearing. Such utility may be provided by adding or laminating additional layers of material to the handle portions, as will be explained in more detail herein.

In an additional preferred mode of the device the handles may be formed of injection molded polypropylene. It is preferred that the polypropylene be thin for flexibility yet provide strength required to withstand the tensile forces associated with the flossing process. Further, in this mode the handle may employ a finger-ingressible aperture or slot as opposed to a slit.

In a particularly preferred mode of the device, the flossing substrate is substantially planar in construction and made of expanded polytetrafluoroethylene (ePTFE). In other preferred modes of the device, the substrate may be multi-filament nylon or non-elastic ultra high molecular weight polyethylene (UHMWPE) or the like. Of course those skilled in the art will realize that other materials may be employed for the substrate and new materials adapted for such may come available. As such, any materials one skilled in the art might employ for the substrate are considered within the scope of this application.

In all preferred modes of the disclosed device, a dissolvable component such as first and second planar edible and dissolvable substrates, dissolvable capsules, or other media adapted to dissolve during use, are engaged at or near an innermost edge of the first and second handle, or in-between them, by an appropriate engagement means. Where the dissolvable component is one or a plurality of dissolvable substrates, they extend from this attachment end to a distal end a distance from the edge of the respective handle.

In other preferred modes of the device, the dissolvable component is provided by one or a plurality of dissolvable capsules having a filled core therein provided and engaged near an innermost edge of the first or second handle by an engagement means or in-between the handles. The capsule or capsules when dissolving are intended to elicit a pleasant gustatory and/or olfactory sensation in the user during use and like the film, may have cores of flavoring, cooling agent, heating agent, dental plaque disclosing agent, or medicine contained in a core or in a solid solution forming the capsule. Additional preferred dissolvable capsule materials are provided below in the detailed description. The dissolvable components may also employ both the film and the capsule should such be advantageous.

The edible substrate, or solid solution formed capsule, may be a pullulan or gelatin base. A pullulan substrate provides a fairly rapid rate of dissolution while a gelatin-based substrate dissolves less quickly and may be desired as well for that reason so as to allow more time for flossing while concurrently communicating a taste and/or cooling sensation to the user during the continued flossing session.

Both edible substrates extend to distal ends spaced from their engagement ends to handles, to a predetermined distance. The preferred two edible substrates cover the flossing substrate extending to connections with the edges of both handles and which determine the distance between the two respective edges of the handles.

In a particularly preferred mode of the device, the edible substrates extend inward from their attachment to the innermost edges of the first and second handles a combined distance that is shorter than the length of the flossing substrate connecting the two handles. This forms a gap between the two opposing distal edges of the first and second edible substrates exposing the flossing substrate therein.

Preferably, the dissolvable edible substrate should be of a vertical width substantially equal to the width of the handles. This maximizes the size of the edible substrate and therefor the time in the mouth required for a total dissolving. The larger size thus provides more time for flossing while concurrently providing the user with encouragement through communicated flavor, cooling agent, medicine or the like. The easy access to the floss therebetween maintains the engagability of the floss substrate between the user's teeth and the subsequent maneuverability within the mouth.

The gap created between the two distal ends of the edible substrate, exposing the flossing substrate, defines an engagement zone in which a saliva-coated tooth or pair of adjacent teeth can engage the flossing substrate without blocking interference from the edible substrate. In use, the flossing substrate is positioned within the space between any two adjacent teeth of a user and the engagement zone provides a means to see the underlying flossing substrate as well as some clearance for the edible substrate during flossing. As flossing commences the edible substrate, situated on both sides of the dental arch, proceeds to dissolve and deliver to the user the desired flavor, cooling agent, medicine, or the like as dictated by the choice of edible substrates. Since edible substrates are positioned on both sides of the gap, and hence both sides of the dental arch during any flossing session, flavor and/or medicine are adequately delivered to all saliva coated teeth and/or saliva coated gum tissue.

In another particularly preferred mode the edible substrates may extend further to a shared abutted edge centrally located on the device. Similarly, the edible substrates may extend even further and overlap about a central position on the device. For both modes, the abutted edge or overlap, the dissolving edible substrates will last longer due to size and might be preferable when used by novice flossers, or by individuals who floss for longer durations. While the underlying flossing substrate may not be initially visible since the gap is eliminated, engagement between the teeth is relatively simple since the distal ends of the edible floss are simply deflected by the teeth upon engagement of the teeth.

In still another particularly preferred mode one or a plurality of portions of edible substrate may be engaged on both surfaces of the device at or near the inner most edge of the handles. In this mode, the opposing layers of the edible substrates extending from the edges of each handle, cover and in effect sandwich the flossing substrate therebetween. As in the longer edible substrate mode, the addition of more edible substrate layers can provide an extended release of flavor, cooling agent, medicine, or breath freshening means as desired by a user or dental health professional. Furthermore, predetermined doses of medicine or the like can be employed on the device as dictated by the amount of edible substrate present on the device. Thus, the device can simultaneously provide a prescribed dose of medicine while promoting proper and continued flossing practice.

With respect to the above description, before explaining at least one preferred embodiment of the herein disclosed invention in detail, it is to be understood that the invention is not limited in its application to the details of construction and to the arrangement of the components in the following description or as illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other oral hygiene structures, methods and systems for carrying out the several purposes of the present disclosed device. It is important, therefore, that the claims be regarded as including such equivalent construction and methodology insofar as they do not depart from the spirit and scope of the present invention.

It is an object of the invention to provide a dental flossing device that provides a gustatory means to encourage a flossing regime through the provision of a dissolvable component such as an edible substrate and/or dissolvable capsule.

It is another object of the invention to provide such a dissolvable component of an edible substrate or dissolvable capsule with one or a combination of a flavoring, cooling agent, medicine, or breath freshening means, or combinations thereof.

It is a further object of the invention to provide a dental device that is easy and comfortable to use for new as well as proficient floss users as well as easy to maneuver in the mouth.

Yet another object of the invention is to provide a discernable engagement zone or gap to define a target to thereby guide a user to the correct position of the device for proper usage.

A further object of the invention is to provide one or a plurality of flossing substrates extending between two handles for use with both the upper and lower set of teeth.

Yet another object of the present invention is the provision of a plurality of any pre-existing commercially available coated, impregnated, waxed, or unwaxed flossing substrate engaged between two handles.

Still a further object of the invention is to provide a neat and convenient packaging for single use employment of the device in a clean, moisture proof environment.

A further object of the present invention is to provide a dental device which is easy to manufacture and commercialize by pre-existing dental floss manufacturers and marketers and retailers of global-branded floss products to better serve end users.

A still further object of the invention is to provide a finger-ingressible communication between both sides of the handles in the form of a slit, slot, or aperture formed in the handle portions of the device to provide for easier finger engagement therewith.

Yet a further object of the invention is to provide such a communication through the handles which employ woven or nonwoven fabric which is adapted to form a splayed engagement of the handle, about the user's thumb or a forefinger for a frictionally enhanced grip therebetween.

Yet another object of the invention herein is the provision of such an improved device, which employs both floss, handles and packaging, which are of recyclable materials.

Further objects of the invention will be brought out in the following part of the specification, wherein detailed description is for the purpose of fully disclosing the invention without placing limitations thereon.

BRIEF DESCRIPTION OF DRAWING FIGURES

FIG. 10b shows a side view of the device from FIG. 10a.

FIG. 11b shows a side view of the device from FIG. 11a.

FIG. 14b shows a side view of the device from FIG. 14a.

FIG. 18a shows, with what is considered a current preferred mode of FIG. 12a depicted, the device showing the formation of a splayed engagement with the surface of the forefinger of the user when tensioned, to prevent slippage, as would be for the first seven steps of the sequence of steps of FIG. 17.

FIG. 18b shows, with what is considered a current best mode of FIG. 12a depicted, an alternate, and optional, preferred eighth step that may be substituted for the first step in the sequence of steps of FIG. 17 which may be further optionally modified, as not shown, for use of the device with the mode of FIG. 12a depicted.

FIG. 20b shows a cross-sectional view of the device of FIG. 20a along line N-N of FIG. 20a.

FIG. 20c shows a cross-sectional view of the device of FIG. 20a along line O-O of FIG. 20a.

FIG. 21b shows a cross-sectional view of the device of FIG. 21a along line P-P of FIG. 21a.

FIG. 22b shows a cross-sectional view of the device of FIG. 22a along line PP-PP of FIG. 22a.

FIG. 24b shows a cross-sectional view of the device of FIG. 24a along line Q-Q of FIG. 24a.

FIG. 24c shows a cross-sectional view of the device of FIG. 24a along line R-R of FIG. 24a.

FIG. 25b shows a cross-sectional view of the device of FIG. 25a along line S-S of FIG. 25a.

FIG. 25c shows a cross-sectional view of the device of FIG. 25a along line T-T of FIG. 25a.

FIG. 25d shows a cross-sectional view of the device of FIG. 25a along line U-U of FIG. 25a.

FIG. 27b shows a cross-sectional view of the device of FIG. 27a along line V-V of FIG. 27a.

FIG. 29b shows a side view of the device from FIG. 29a.

DETAILED DESCRIPTION OF THE PREFERRED EMBODIMENTS OF THE INVENTION

Figure 1A:
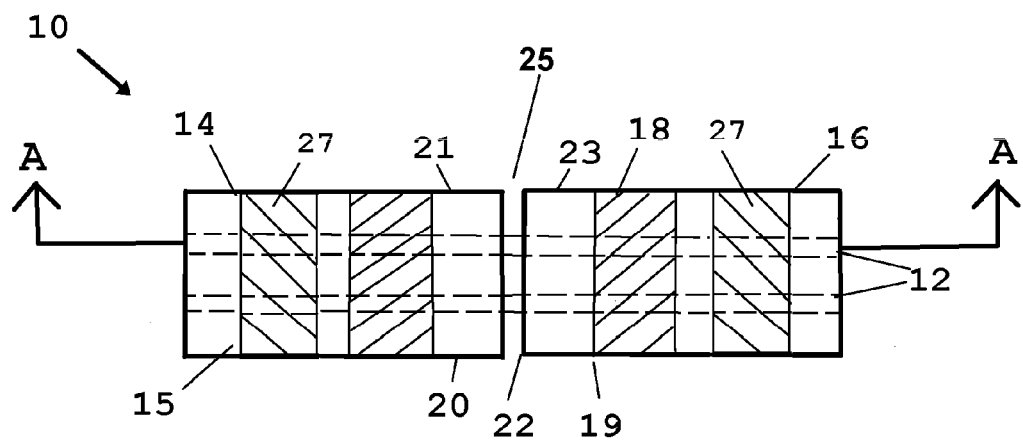
FIG. 1a shows a top plan view of a particularly preferred mode of the device showing a side surface and a gap.

Now referring to drawings in FIGS. 1-30, wherein similar components are identified by like reference numerals, there is seen in FIG. 1a a particularly preferred mode of the device 10. In this mode a left and right handle 14 and 16 are shown engaged to flossing substrate 12 communicating therebetween and providing means for engagement with the one or more fingers in a substantially frictional engagement by a user during use.

Also extending from an attachment point to each handle 14 and 16, from the same respective edge thereof where the flossing substrate 12 extends, are dissolvable components formed by a first portion 21 and second portion 23 of a dissolvable component provided by an edible substrate 20 material which is adapted to dissolve when contacted by saliva coated teeth and gums. The edible substrate 20 portions 21 and 23, are sized to extend from their attachment point to their respective handle 14 and 16, a distance less than the total length of the flossing substrate 12 extending therebetween. Consequently when the handles 14 and 16 are engaged by one or a plurality of fingers of a user in the as-used position (FIGS. 16, 17, and 18), and the flossing substrate 12 is taught, a gap 25 is centrally located between the terminating ends of the first portion 21 and second portion 23 of the edible substrate 20 which defines an engagement zone 22 for the device 10. The engagement zone 22 provides a clearance and a visual targeting means for a user to properly position the device 10 to engage the flossing substrate 12 in the space between two adjacent teeth when a user is employing the device 10 in the as-used position to clean their teeth in a flossing procedure.

The sizing of the portions of the dissolvable components formed as flavored edible substrate 20 are configured to form the length of the flossing substrate 12 to define the gap 25 and engagement zone 22, thereby provides users a targeting means and is particularly preferred. The targeting means so formed allows users an easy means to visually ascertain the proper positioning of the device 10 and flossing substrate 12 when held by the handles 14 and 16, to properly engage and employ it in a flossing session.

Colorizing the edible substrate 20 or other dissolvable component employed, provides a means for increasing the ability of the user to discern the gap 25 and the engagement zone 22 since the gap 25 will be void of the color. As such, providing colored edible substrate 20 will even allow users requiring glasses or contacts for close viewing to ascertain the proper position for engagement of the device 10 with their teeth, without their eyewear. For instance using a color or dye that fluoresces under room light or is otherwise bright, will cause the gap 25 to visually stand out against the two adjacent portions 21 and 23, of the edible substrate 20.

Those skilled in the art will realize that in the employment of flossing substrate 12 in the proper length between the handles 14 and 16 to form the gap 25 along with the appropriately sized edible substrate portions 21 and 23 of the edible substrate 20, they may be engaged to the handles 14 and 16 in any number of fashions. All such means of engagement as would so occur, are considered to be within the scope of this application.

Figure 1B:
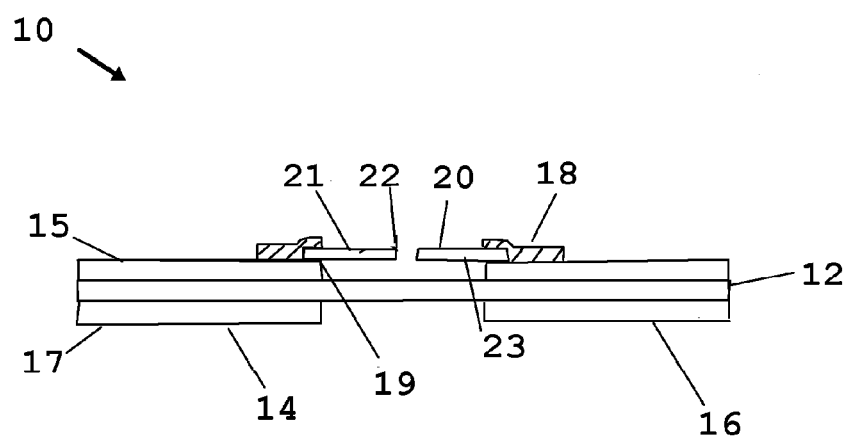
FIG. 1b shows a cross-sectional view of the device of FIG. 1a as seen along line AA.

One preferred mode of such attachment is shown in FIGS. 1a-1b, where the handles 14 and 16 are depicted with top and bottom planar portions 15,17 of a flexible hypoallergenic material. The preferred hypoallergenic material for the handles 14 and 16 may also have a friction enhancing adherent 27 positioned upon the exposed surfaces to increase the frictional engagement with the user's finger during tensioning of the flossing substrate 12 while employing the device 10 in the as-used position. Since the handles 14 and 16 can easily become wet or damp during the process, a friction enhancement with the surface of one or more fingers to the surfaces of the handles 14 and 16 would be preferred. Currently preferred adherable friction enhancing materials for the adherent 27 can be one or a combination of such materials from a group including a tackified adhesive, a re-adherable adhesive, a non-tackified adhesive, a heat sealant adhesive, beeswax, carnauba wax, jojoba wax, *Commiphora myrrha* resin extract, propolis cera, and a rubbery hot-melt adhesive. Tackified adhesives currently favored are acrylate adhesive or polybutylacrylate. However, any tackified or non-tackified adhesive as would occur to those skilled in the art upon reading this specification is anticipated within the scope of this patent.

One favored material for forming the handles 14 and 16 is available commercially as product number 1538 from the 3M Company. Another such material which is a particularly preferred fabric for the handles is a nonwoven fabric from Dupont sold under the tradename TYVEK which is fully recyclable. TYVEK 1059B is the preferred grade of TYVEK fabric. However, the material can be any woven or nonwoven fabric suitable to the described task herein such as a spunbonded high density polyethylene. Either of these materials, or any material one skilled in the art might choose, would benefit in the damp environment of flossing from the increased frictional engagement with the one or more of the user's fingers during tensioning of the floss substrates 12 in the as-used position, by positioning the friction enhancing surface thereon as noted above.

One, or more preferably a plurality of flossing substrates 12, sized to form the gap 25, extend between respective engagements to each of the handles. A particularly preferred means to engage the flossing substrate 12 to the handles 14 and 16, is by sandwiching the substrate 12 between the inner surfaces of the top and bottom planar portions 15,17 of the handles 14,16. The top and bottom portions would be engaged using a tackified adhesive, molding, or other means to engage them in a manner to hold the flossing substrate 12 engaged therebetween.

As noted, a particularly preferred mode of the device 10 in all depicted modes, employs dissolvable components in the form of a plurality of flossing substrates 12 shown as two flossing substrates 12. Particularly preferred for ease of insertion between teeth, is a planar flossing substrate material formed of a shred-proof friction-lessening material such as expanded polytetrafluoroethylene (ePTFE). Alternatively, the device 10 may employ flossing substrate portions formed of multi filament nylon or a non-elastic ultra high molecular weight polyethylene (UHMWPE). The flossing substrate employing ePTFE, or nylon, or UHMWPE may be waxed, coted, impregnated, Auxetic or unwaxed flossing substrates.

The two sections of flossing substrate 12 employed on the device 10 may be similar in construction, or may employ different substrate types as desired by a user. However, due to the superior coverage a plurality of flossing substrates 12 provides during translation over the surface of teeth during flossing, the provision of at least two flossing elements 12 is more desirable so as to aid a user in properly removing undesirable material from the surfaces of teeth being flossed.

A view from cross-sectional cut AA is seen in FIG. 1b. The dissolvable components shown as edible and preferably flavored edible substrate 20 or dissolvable component portions, suitable for dissolution in liquid and especially saliva, are shown as a first and second portion respectively 21, and 23. In one particularly preferred manner for all modes of the device 10 the edible substrate 20 is pullulan based to provide a means for rapid dissolution in the mouth during use. Also, the substrates 20 are formed in substantially rectangular shape. However, those skilled in the art can appreciate a multitude of shapes and forms that can be employed which achieve the same goal and are anticipated by this application.

The edible substrate portions 21,23 are shown on the first or top planar portion 15 of the device 10 at or near the innermost edges 19 of the handles 14,16 where the flossing substrate 12 communicates therebetween. As noted, a means for engagement of the edible substrate 20 may be achieved through the provision of secondary adhesive cloth tape 18, shown by hatched fill lines in the figure, engaging the dissolvable component provided by the edible substrate 20 to the first or top planar portion 15 at or near the innermost edge 19 of the respective handles. Of course other means for engagement for the edible substrate 20 may be employed and any such means of engagement as would occur to those skilled in the art is anticipated within the scope of this patent.

So engaged using adhesive or other means of engagement, the first and second portions 21,23 of the edible substrate 20 extend inward along one side surface of the flossing substrate 12 which communicates between the engaged handles. As noted, shown in a particularly preferred mode, are the edible substrate 20 portions extending to distal ends insofar as to maintain the gap 25 centrally located on the device 10 in the as-used position with the flossing substrates 12 taught between the handles, and thereby defining the engagement zone 22.

Figure 2:
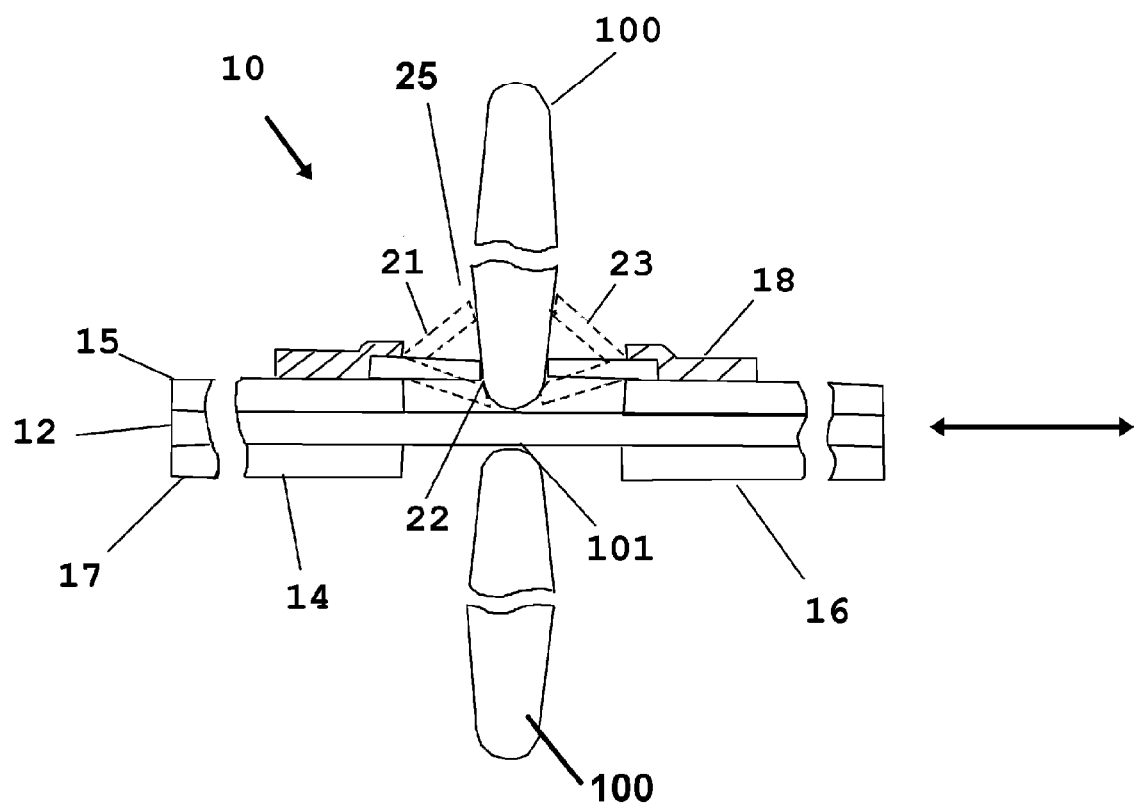
FIG. 2 is a cross-sectional view of the device of FIG. 1a, as seen along line AA thereof, depicted in an as-used position, as wherein the device is engaged in a space between two adjacent incisors.

This clearance is shown in FIG. 2 which depicts a top cross-sectional view of the device 10 in an as-used position. The device 10 is shown with the flossing substrate 12 engaged within the gap 101 between two adjacent incisors 100. The engagement zone 22 provides clearance for the first and second portions 21,23 of the edible substrate 20 from the adjacent incisors 100. Additionally the gap 25 defines a means for targeting the floss substrates 12 to a position proximate to the gap 101 between any two adjacent teeth of the user whereafter the floss substrates 12 may be slidably engaged into the gap 101 more easily.

Using conventional translational flossing motion, the edible substrate portions 21,23 are deflected by the incisors and as shown deflected by incisor 100. Concurrently the substrate portions 21 and 23 providing the dissolvable components, continually dissolve thereby depositing one or a combination of wet or dry ingredients upon the teeth, gums, and surrounding mouth of the user. Whether the capsule or edible substrate or combinations thereof, the dissolvable components can include one or a combination of wet or dry ingredients from a group including, a dissolvable component formed as a solid solution such as dissolvable candies and mints, or a dissolvable capsule containing a core formed of one or a combination of wet or dry materials from a group including, a breath freshening core, a medicinal dosage, nutritional supplements, flavoring, mouthwash, a cooling agent, a heating agent, a dental plaque disclosing agent, a medicine and nutritional supplements. Further for either mode of dissolvable component included, it may be desirable to employ a means to slow the rate of dissolution thereof. For instance when employing the edible substrate portions 21 and 23, or capsule 90, a slower dissolving rate for slower flossing users such as children, and this may be accomplished in a number of ways known to those skilled in the art, for instance using a mixture of 76% gelatin base for the edible substrates 21 and 23 or capsule 90.

Figure 3:
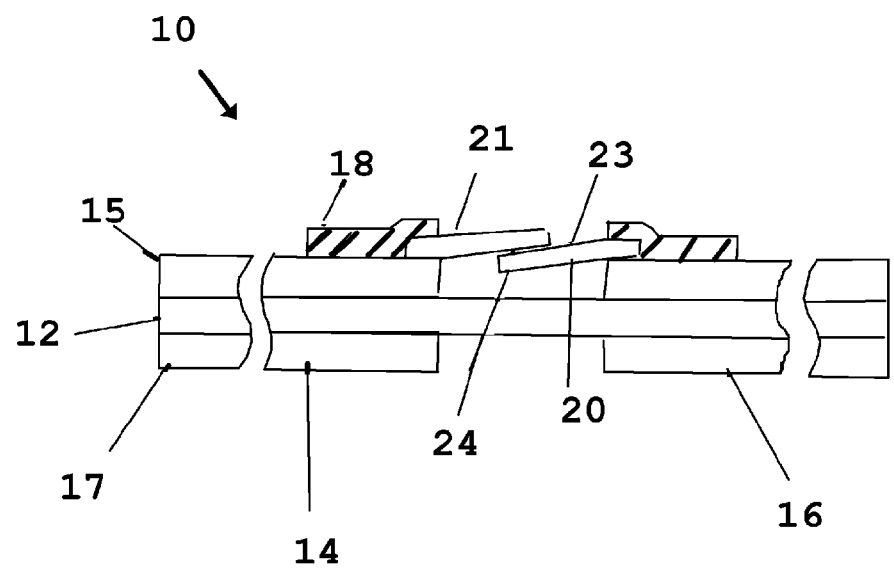
FIG. 3 shows a cross-sectional view of another particularly preferred mode of the device depicting an overlap of the edible substrates covering one side view of the gap and flossing substrate therein.

Another particularly preferred mode of the device 10 can be seen in the cross sectional view in FIG. 3. Similar to that of the mode described in FIGS. 1a and 1b, construction of device 10 employs an attachment of the handles 14 and 16 to the dissolvable component or edible substrate 20 and the flossing substrate 12. In the depicted mode of the device 10 in FIG. 3, the first and second edible substrate portions 21,23 extend insofar to create an overlap 24 of the first and second portions. This mode of the device 10 provides an increased portion of edible substrate 20 which can be deposited in the mouth of the user. Upon engagement of the flossing substrate 12 to a pair of adjacent teeth (not shown) the portions 21,23 are simply deflected away. While the preferred gap 25 is not employed for targeting, the overlap point of the substrate portions 21 and 23 may also be employed, or, the two substrate portions 21 and 23 may be formed of different colors to enhance the overlap as the targeting position for engagement to the teeth by the user.

Figure 4:
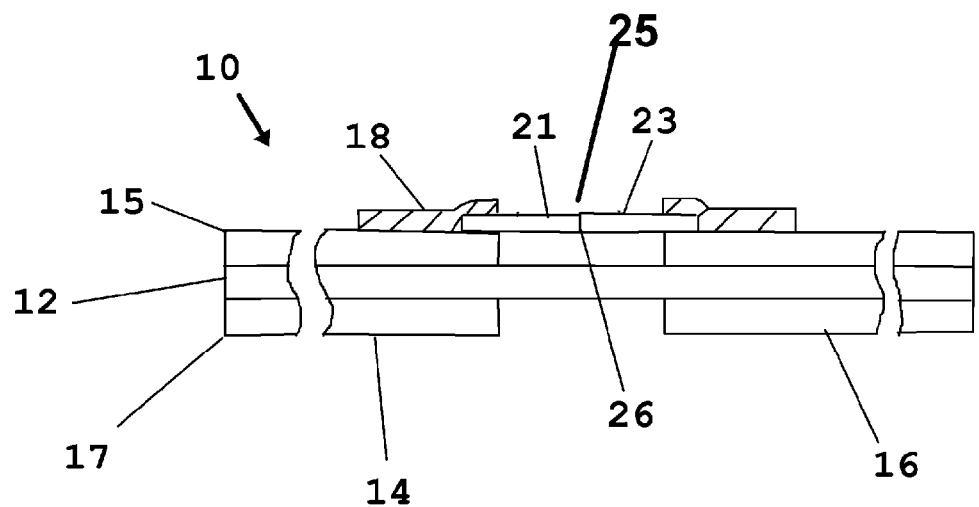
FIG. 4 shows a cross-sectional view of yet another particularly preferred mode of the device depicting the edible substrates extending inward to a shared abutment of their distal ends.

Yet another preferred mode of the device 10 is seen in a similar cross sectional view in FIG. 4. While similar in construction and use to the device of FIGS. 1a and 1b, this mode of the device 10 employs the first and second edible substrate portions 21 and 23, having a length which provides for abutting distal ends 26 at the gap 25 which may be used for targeting at engagement with the user's teeth. The position of the gap 25 may be enhanced using different color substrate portions 21 and 23, or by terminating the colorizing of the substrate portions 21 and 23 just before their distal ends 26 thereby forming a virtual gap 25 viewable by the users for targeting the device 10 for insertion between their teeth during flossing.

Figure 5A:
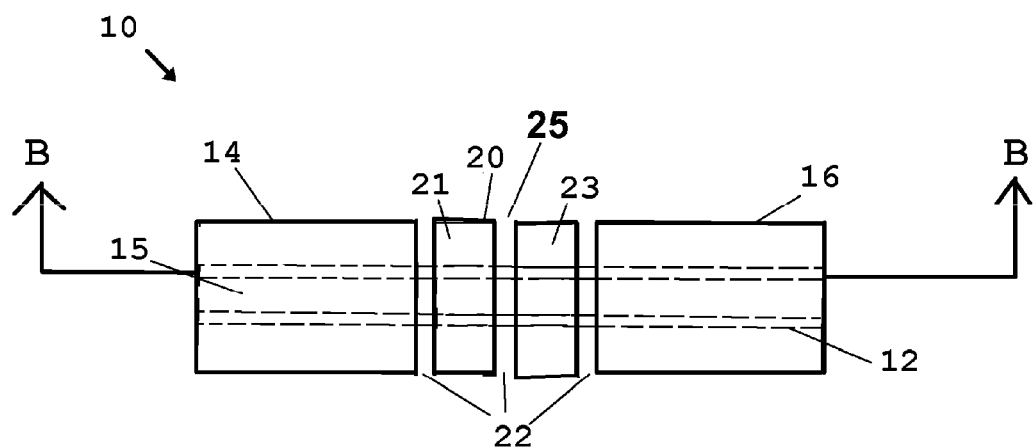
FIG. 5a is a top plan view of still another preferred mode of the disclosed device depicting dissolvable components in the form of edible substrates engaged on both surfaces of two flossing substrates with a plurality of engagement zones therein.
Figure 5B:
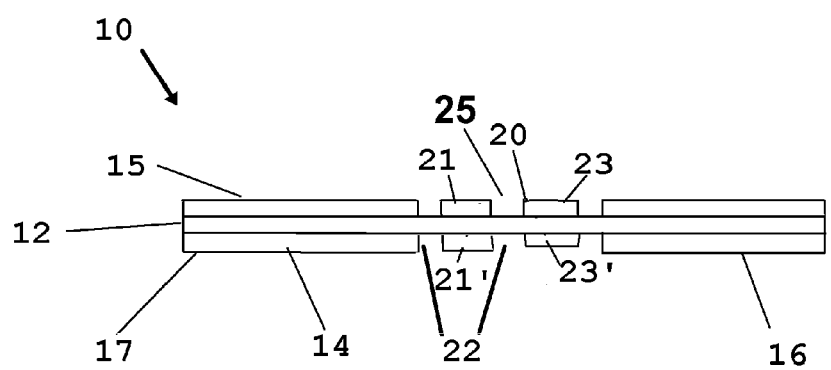
FIG. 5b is a side cross-sectional view of the device of FIG. 5a seen from line BB.

A further mode of the device 10 is shown in FIG. 5a and side cross-sectional view about line BB shown in FIG. 5b. Employing similar construction and means of engagement of the left and right handles 14,16 with the flossing substrate 12 as that of FIG. 1, this mode employs first and second substrates 21 and 23 in a sandwiched engagement with opposing first and second portions 21',23' of edible substrate 20, upon the flossing substrate 12.

The first and second portions 21,23 shown positioned between the innermost edges 62 of the first or top planar portion 15 of the handles 14, 16 are respectively joined by an engagement means to the opposing first and second portions 21',23', similarly positioned between the innermost edges 64 of the second or bottom planar portion 17 of the handles 14, 16, thereby providing a means to hold them in place on the flossing substrate 12. Means to mate the portions of the top and bottoms surfaces may include one or a combination of edible adhesives or by simply wetting the substrates and allowing them to dry after applying contact pressure on the two portions. For the configuration shown in the figure a plurality of engagement zones 22 are created, and allow for a plurality of targeting or initiation positions to be employed by the user when engaging the flossing substrate 12 between teeth.

Figure 6A:
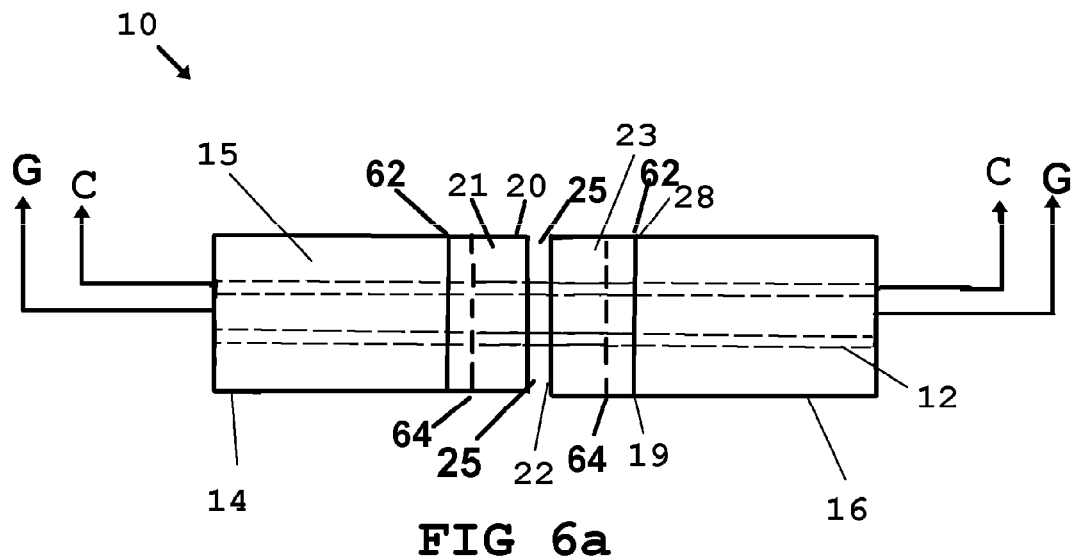
FIG. 6a depicts what is currently considered a preferred mode of the device showing a top plan view and a layer of edible substrate extending from handles.
Figure 6B:
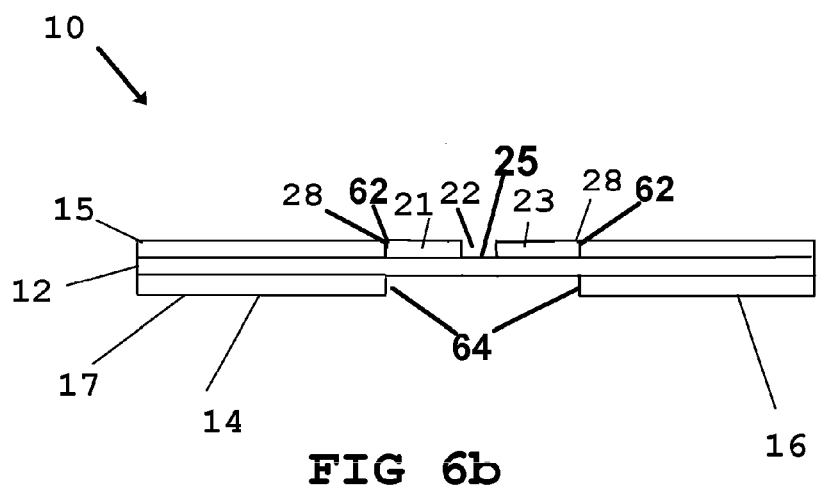
FIG. 6b shows a cross-sectional view of the device of FIG. 6a seen from line CC.
Figure 6C:
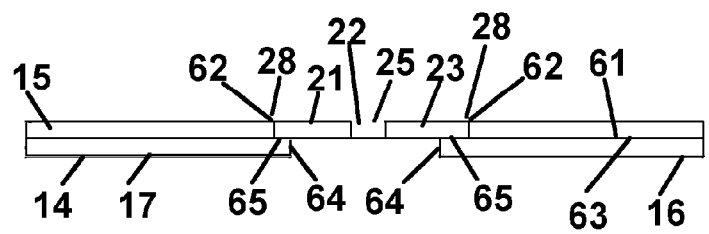
FIG. 6c depicts a cross-sectional view of the device along line G-G.

A preferred mode of the device 10 is shown in FIGS. 6a, 6b and 6c. As evidenced from FIGS. 6a, 6b and 6c, the first or top planar portion 15 has, as shown in FIG. 6c, an inner most surface 61 and the second or bottom planar portion 17 has an inner most surface 63. As further evidenced in FIG. 6c, and therein on each handle 14 and 16, first and second portions 21, 23 of edible substrate 20 are engaged respectively on a ledge or an inner most portion 65 of the inner most surface 63 of the second or bottom planar portion 17 thereof, thereby joining the respective portions 21 and 23 of edible substrate 20 to handles 14, 16.

As even further evidenced in FIGS. 6a, 6b and 6c, first and second portions 21, 23 of edible substrate 20 are engaged respectively on the handles 14 and 16 at the inner most edges 62 of the first or top planar portion 15 of the handles 14 and 16 at the respective abutted edges 28 shared therebetween. As evidenced in FIG. 6c, each inner most edge 64 of the second or bottom planar portion 17 of each respective handle 14 and 16 is longitudinally spaced apart from the inner most edge 62 of the first or top planar portion 15 to form a ledge or an inner most portion 65 on an inner most surface 63, on each handle 14 and 16. As in the device of FIG. 1, a gap 25 defining a means for targeting or an engagement zone 22 is formed in a centrally located position on the device 10 providing the target for means of engagement of the device 10 for use. As shown in FIGS. 6a, 6b and 6c, the device 10 represents a preferred mode of the invention, and the device 10 represents the most efficient structure employing the least amount of the flexible and hypoallergenic adhesive cloth tape and the like employed in the handles 14, 16.

Figure 7A:
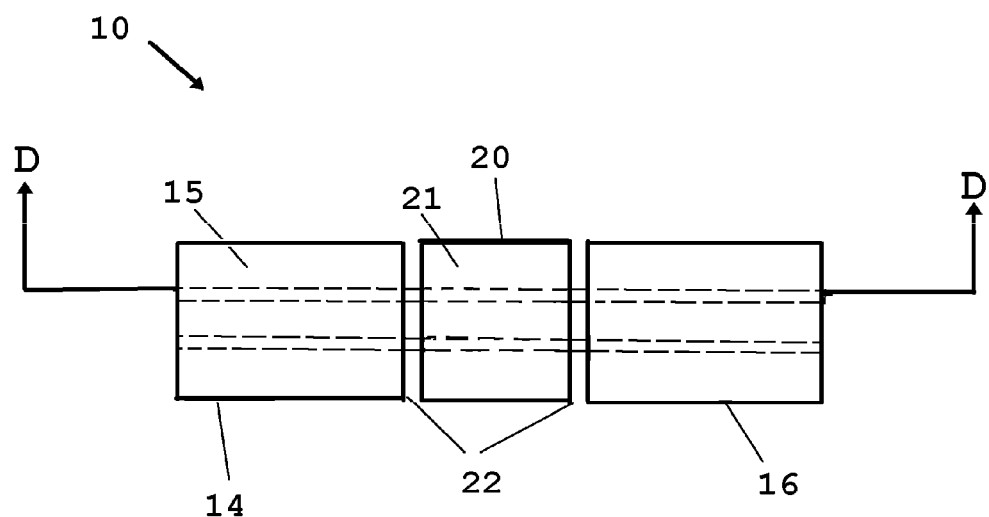
FIG. 7a is another preferred mode of the device depicting the edible floss engaged to the parallel flossing substrates communicating between two handles.
Figure 7B:
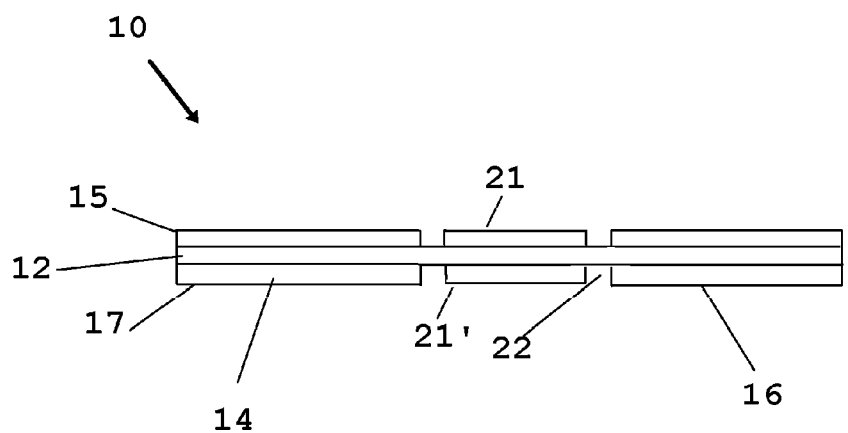
FIG. 7b shows a cross-sectional view of the device of FIG. 7a seen from line DD.

Still a further particularly preferred mode of the device is seen in FIGS. 7a and 7b. A substantially larger edible substrate 20 is engaged with a first portion 21 on the flossing substrate 12 positioned substantially midway between the innermost edges 62 of the first or top planar portion 15 of the first 14 and second 16 handles respectively. Further, a second portion 21' of edible substrate 20 is positioned on the flossing substrate 12 substantially midway between the innermost edges 64 of the second or bottom planar portion 17 of the first 14 and second 16 handles respectively. The two portions of edible substrate 20 are held in place on the flossing substrate 12 by means of engagement such as adhesive or by engagement of the material forming the substrate portions. Gaps providing multiple engagement zones 22 for targeting during use are maintained near both the first and second handles 14,16.

Figure 8A:
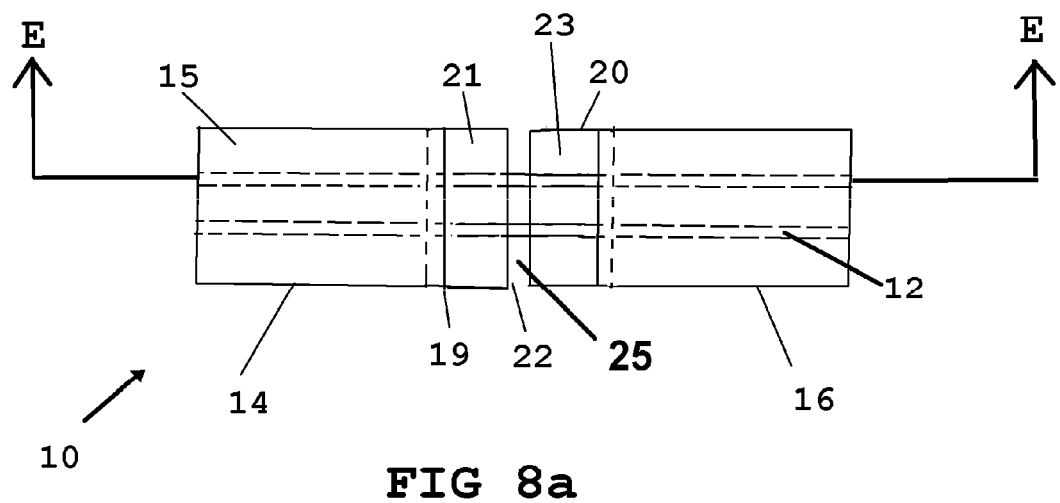
FIG. 8a is a further preferred mode of the device having multiple layers of edible substrate extending from an engagement to each handle on opposite sides of the floss.
Figure 8B:
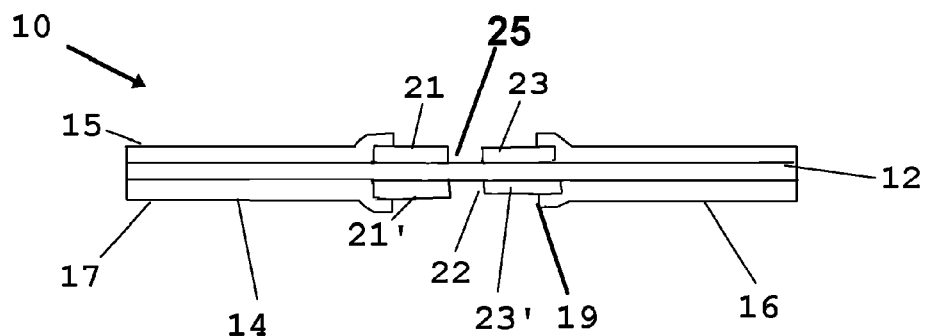
FIG. 8b shows a cross-sectional view of the device of FIG. 8a seen from line EE.

Another preferred mode of the device is shown in FIGS. 8a and 8b. In this mode first and second portions 21,23 of edible substrate 20 adjacent the top planar portion 15 and first and second portions 21',23' of edible substrate adjacent the bottom planar portion 17 are engaged to the respective handles 14,16 at the inner most edge 19 by a surrounding means of engagement. Such an engagement means may be a substantial overlap at the edge 19 of the two opposing portions of material forming the handles themselves thereby adhering or engaging the edible substrate 20 in a manner for it to extend toward the opposite handle and over the flossing substrate 12. Again, a gap 25 forming the target or engagement zone 22 is maintained.

Figure 9A:
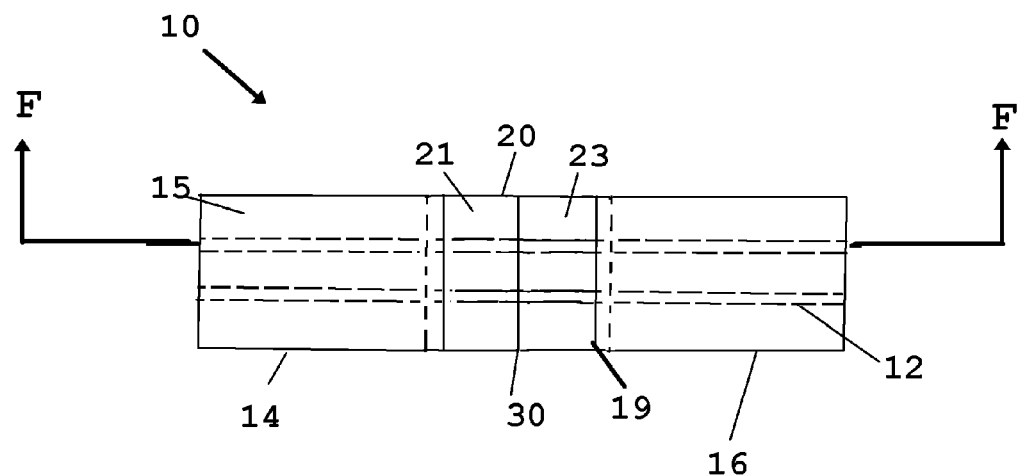
FIG. 9a shows another preferred mode of the device having multiple layers of an edible substrate which abut each other on opposite sides of the floss substrate.
Figure 9B:
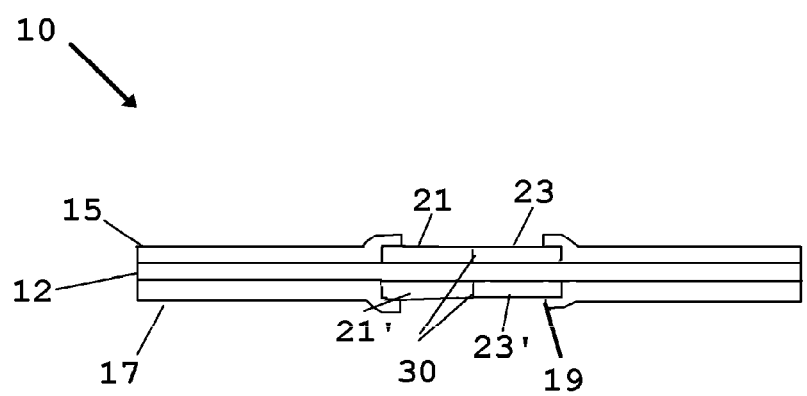
FIG. 9b shows a cross-sectional view of the device of FIG. 9a seen from line FF.

FIGS. 9a and 9b show still another mode of the device 10 similar to that of FIGS. 8a and 8b except that the first and second portions of edible substrate 20 of both the top and bottom surface 21,23,21',23' extend toward respective opposite handles to respective abutted edges 30 forming the target defining an engagement zone for the user during use, as opposed to leaving the gap defining the engagement zone 22 previously described.

Figure 10A:
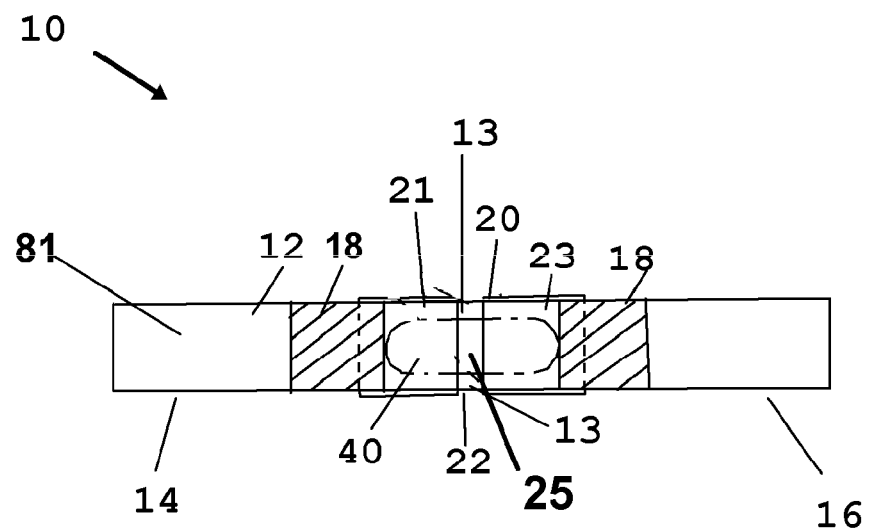
FIG. 10a is still another mode of the device.
Figure 10B:
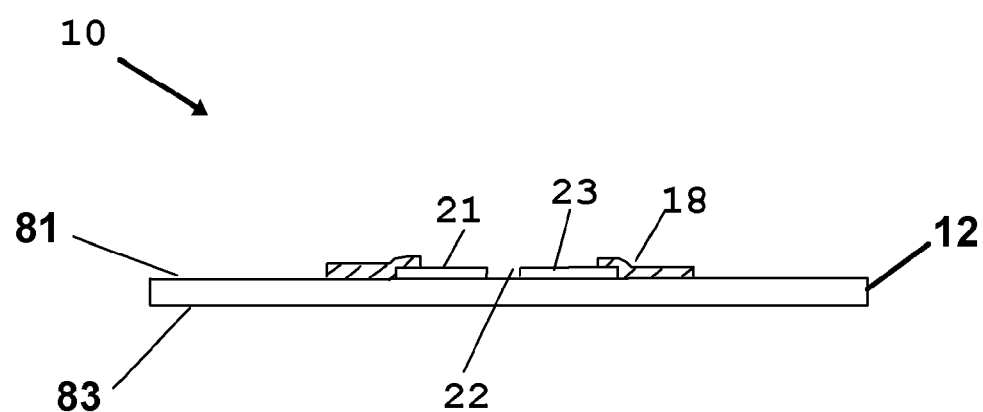

FIGS. 10a and 10b show an additional mode of the device 10 configured by a flossing substrate 12 with an aperture 40 formed communicating between the first or top planar surface 81 and a second or bottom planar surface 83. First and second handles 14,16 are defined by end portions of the planar flossing substrate 12. Side portions 13 of the planar flossing substrate 12 extend around the perimeter of, and help define the aperture 40, and preferably align with the edge of the adjacent substrate 12 thereby providing an elongated means to floss when engaged within the crevices between teeth.

First and second portions 21,23 of edible substrate 20 are engaged on one surface such as the first or top planar surface 81 of the device by operative means of engagement. Engaged to the flossing substrate 12, portions 21,23 are cut or formed in a manner to overlap the aperture 40 and have the same side edge, that is widths, as the flossing substrate 12. The portions 21,23 are engaged at or near the ends of the aperture 40 using means of engagement such as adhesive or tape 18. The portions 21, and 23 extend inward and over the aperture 40. The gap 25 is maintained between the two portions and defines the target for the user in the engagement zone 22 as previously described.

Figure 11A:
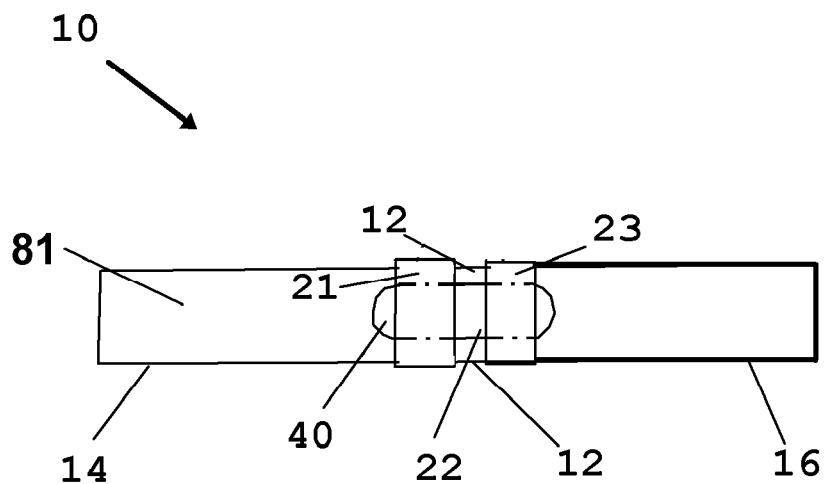
FIG. 11a shows another mode of the device.
Figure 11B:
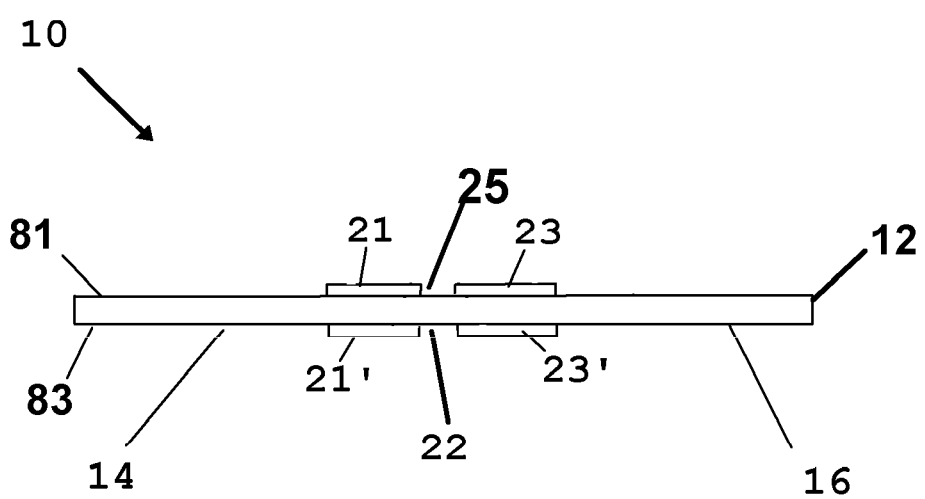

An additional mode of the device 10 is depicted in FIGS. 11a and 11b. First and second portions 21,23 of edible substrate 20 positioned on both the first or top planar surface 81 are respectively joined by an engagement means to the first and second portions 21',23' on the opposing second or bottom planar surface 83 holding them in place over the aperture 40. Means to mate the portions of the top and bottom surfaces may include one or a combination of edible adhesives or by simply wetting the substrates and allowing them to dry after applying contact pressure on the two portions.

Figure 12A:
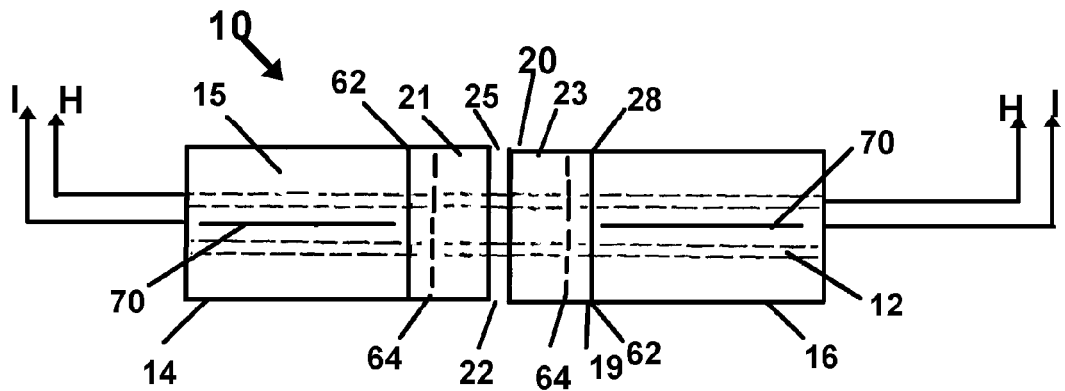
FIG. 12a depicts what is considered a current particularly preferred mode of the device showing a top view and a layer of edible substrate extending from handles that each have a slit or aperture.
Figure 12B:
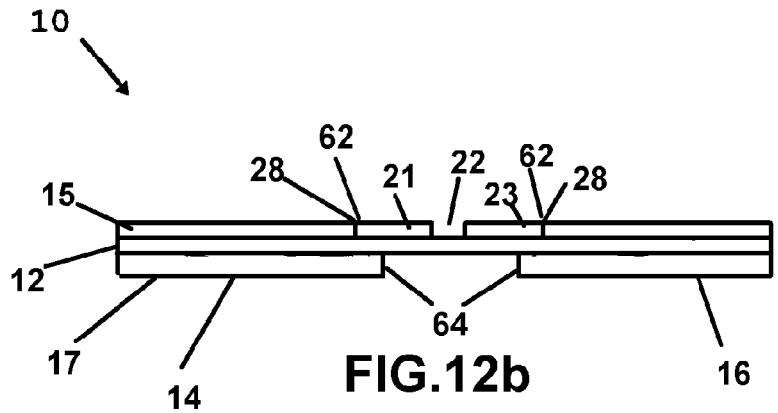
FIG. 12b shows a cross-sectional view of the device of FIG. 12a seen from line HH.
Figure 12C:
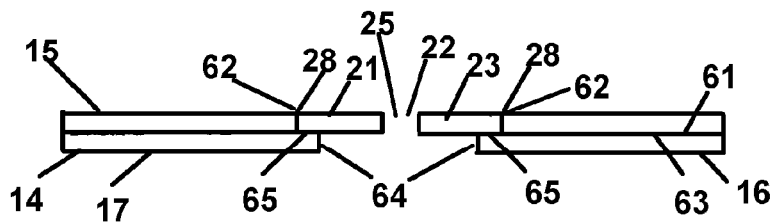
FIG. 12c shows a cross-sectional view of the device of FIG. 12a as seen from line II.

A particularly preferred current mode and the most preferred mode of the device 10 is shown in FIGS. 12a, 12b and 12c. FIGS. 12a, 12b and 12c respectively show views of the device 10 similar to but further modified from FIGS. 6a, 6b and 6c. The structure of the device 10 from FIGS. 12a, 12b and 12c is identical to the structure of the device 10 in FIGS. 6a, 6b and 6c except for a transversely centered and longitudinally centered longitudinal slit or aperture 70 within each handle 14, 16 of device 10. In this best current mode of the device 10, each handle 14, 16 is dimensioned large enough so that each longitudinal slit or aperture 70 in each handle 14 and 16 is dimensioned large enough to be capable of being easily penetrated by the forefinger, and each handle 14 and 16 is dimensioned large enough to be capable of being held and tensed to a useful degree of tension with forefingers as occurs during an alternate kind of flossing session. Such a slit or aperture 70 in each handle 14, 16 of the device 10 can be incorporated to alternately, and optionally, modify the structure of any other mode of the invention.

Figure 13A:
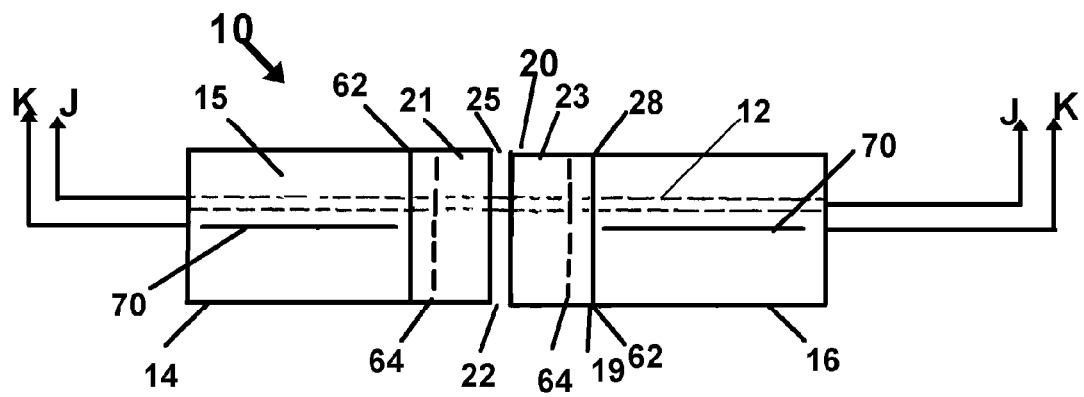
FIG. 13a is yet another preferred mode of the device with a single flossing strand showing a top view and a layer of edible substrate extending from handles that each have a slit or aperture.
Figure 13B:
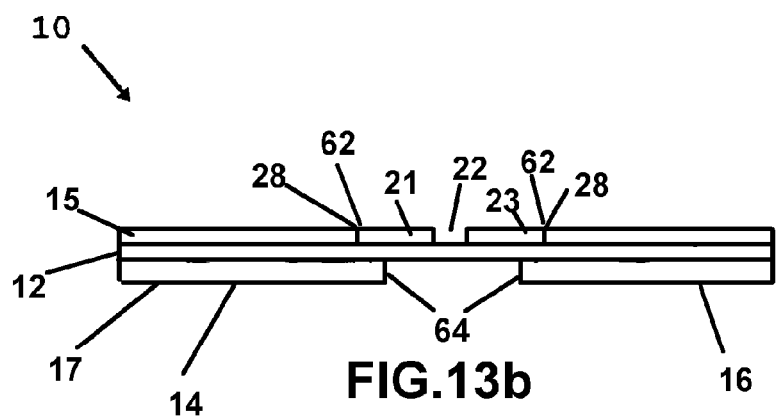
FIG. 13b shows a cross-sectional view of the device of FIG. 13a seen from line JJ.
Figure 13C:
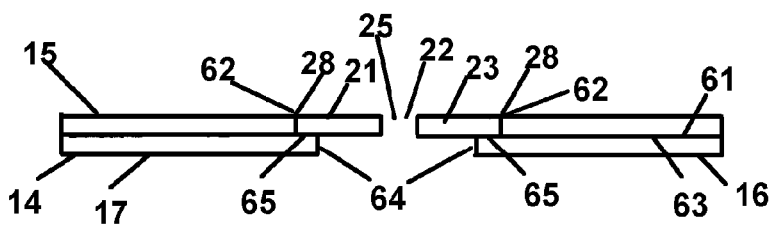
FIG. 13c shows a cross-sectional view of the device of FIG. 13a as seen from line KK.

A still further embodiment of another preferred mode of the device 10 is shown in FIGS. 13a, 13b and 13c. FIGS. 13a, 13b and 13c respectively show views of the device 10 similar to FIGS. 12a, 12b and 12c. The structure of the device 10 from FIGS. 13a, 13b and 13c is identical to the structure of the device 10 in FIGS. 12a, 12b and 12c except for a single strand of flossing substrate 12 is employed between the handles 14,16. There is further shown a transversely centered and longitudinally centered longitudinal slit or aperture 70 within each handle 14, 16 of device 10. In this preferred mode of the device 10 similar to that of FIGS. 12a-c, each handle 14, 16 is dimensioned large enough so that each longitudinal slit or aperture 70 in each handle 14 and 16 is dimensioned large enough to be capable of being easily penetrated by the forefinger, and each handle 14 and 16 is dimensioned large enough to be capable of being held and tensed to a useful degree of tension between or about forefingers as occurs during an alternate kind of flossing session. Again, such a slit or aperture 70 in each handle 14, 16 of the device 10 can be incorporated to alternately, and optionally, modify the structure of any other mode of the invention.

Figure 14A:
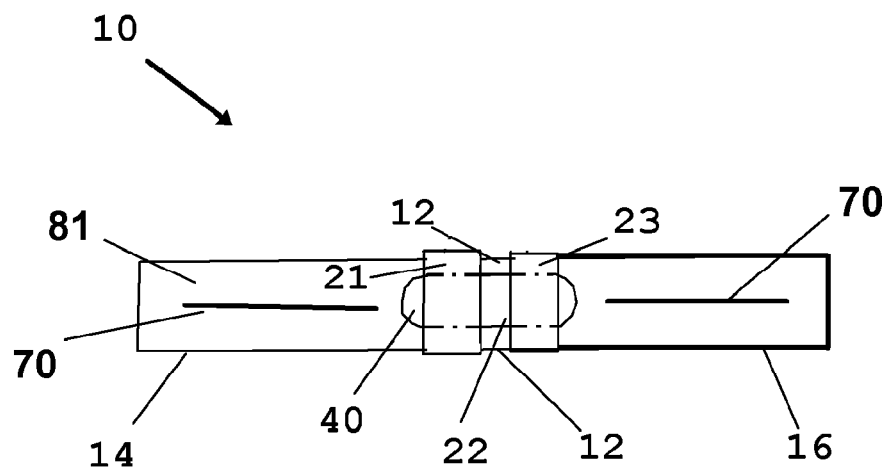
FIG. 14a shows another mode of the device similarly having a slit or aperture formed to communicate through the handles.
Figure 14B:
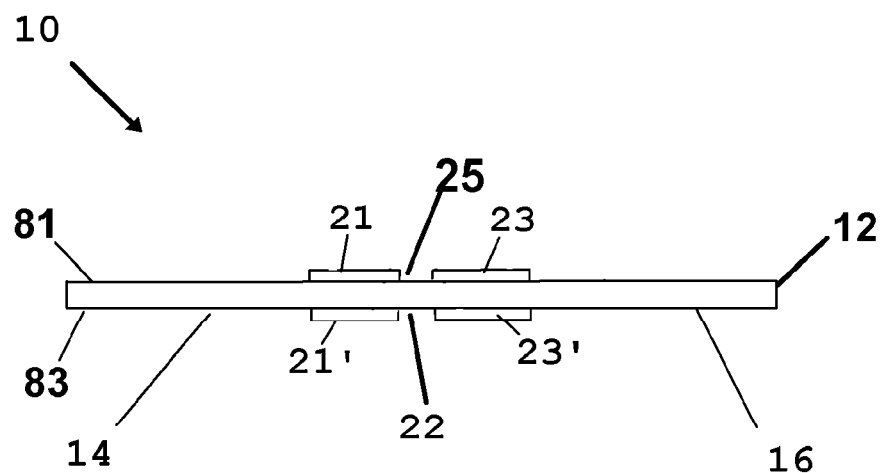

A yet still further embodiment of a particularly preferred mode of the device 10 is depicted in FIGS. 14a and 14b. FIGS. 14a, 14b respectively show views of the device 10 similar to but further modified from FIGS. 11a, and 11b. The structure of the device 10 from FIGS. 14a and 14b are identical to the structure of the device 10 in FIGS. 11a and 11b except for a transversely centered and longitudinally centered longitudinal slit or aperture 70 within each handle 14, 16 of device 10. First and second portions 21,23 of edible substrate 20 positioned on both the first or top planar surface 81 are respectively joined by an engagement means to the first and second portions 21',23' on the opposing second or bottom planar surface 83 holding them in place over the aperture 40. Means to mate the portions of the top and bottom surfaces may include one or a combination of edible adhesives or by simply wetting the substrates and allowing them to dry after applying contact pressure on the two portions.

Figure 15A:
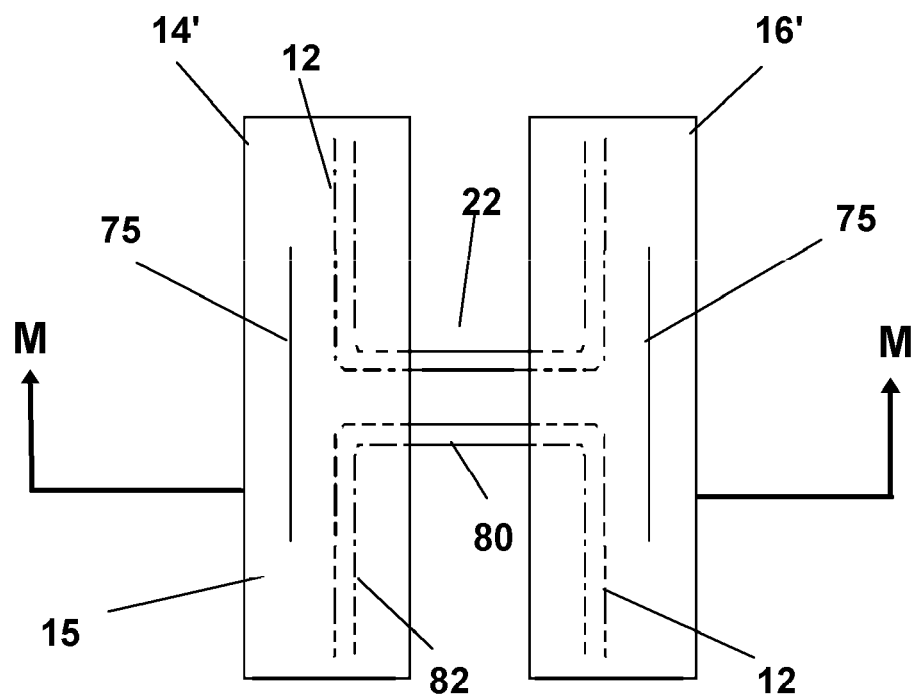
FIG. 15a shows still yet another mode of the device having a slit or aperture disposed in the transverse direction.
Figure 15B:
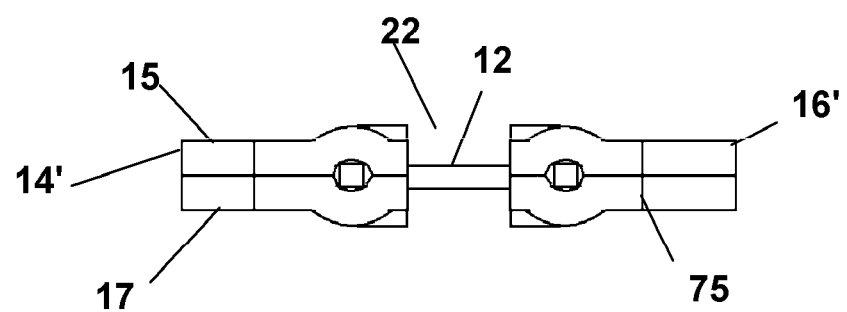
FIG. 15b shows a cross sectional view of the device from FIG. 15a as seen from line MM.

A still further embodiment of the preferred mode of the device 10 is depicted in FIGS. 15a and 15b. In this mode the handles 14',16' are disposed in the transverse direction including a transversely centered slit or aperture 75 within each handle 14',16' of the device 10. The flossing substrate 12 is again shown sandwiched between a first or top planar portion 15 and second or bottom planar portion 17. As can be seen the flossing substrates 12 communicate through the engagement zone 22 between the handles 14',16' disposed substantially parallel in the longitudinal direction 80. Upon sandwiched engagement with the top 15 and bottom 17 planar portions of the handles 14',16' the substrate 12 then extends substantially at a right angle in a disposition parallel to the transverse direction 82. This mode may better provide a means to maintain the substrate 12 in sandwiched engagement between the portions 15,17 of the handles 14',16' when a user applies tension in the longitudinal direction as is in the as used mode. Further, this mode may additionally be modified to employ the edible substrates 21,23 of any of the previously disclosed preferred modes of the device 10.

Figure 16:
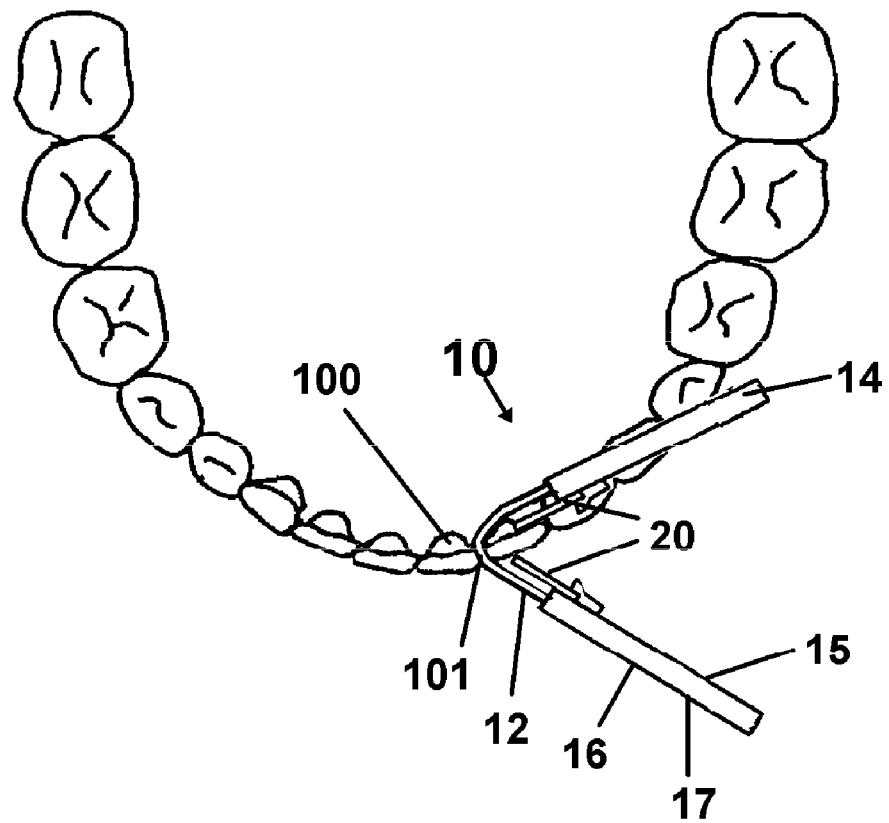
FIG. 16 is a top view of the device depicted in an as-used position between two adjacent teeth and shown translatabley engaged within the space between a pair of incisors.

FIG. 16 shows a top view of the device 10 from FIGS. 1a and 1b in the as-used position translatabley engaged for flossing. The flossing substrate 12 is shown engaged within the space 101 between two adjacent incisors 100. The edible substrate 20 is positioned near the incisor 100 and as contact with a saliva coated tooth or gum tissue begins, dissolvable component provided by the substrate 20 proceeds to dissolve and deposit any of the aforementioned ingredients flavor, cooling agent, medicine, etc. or combination thereof.

Figure 17:
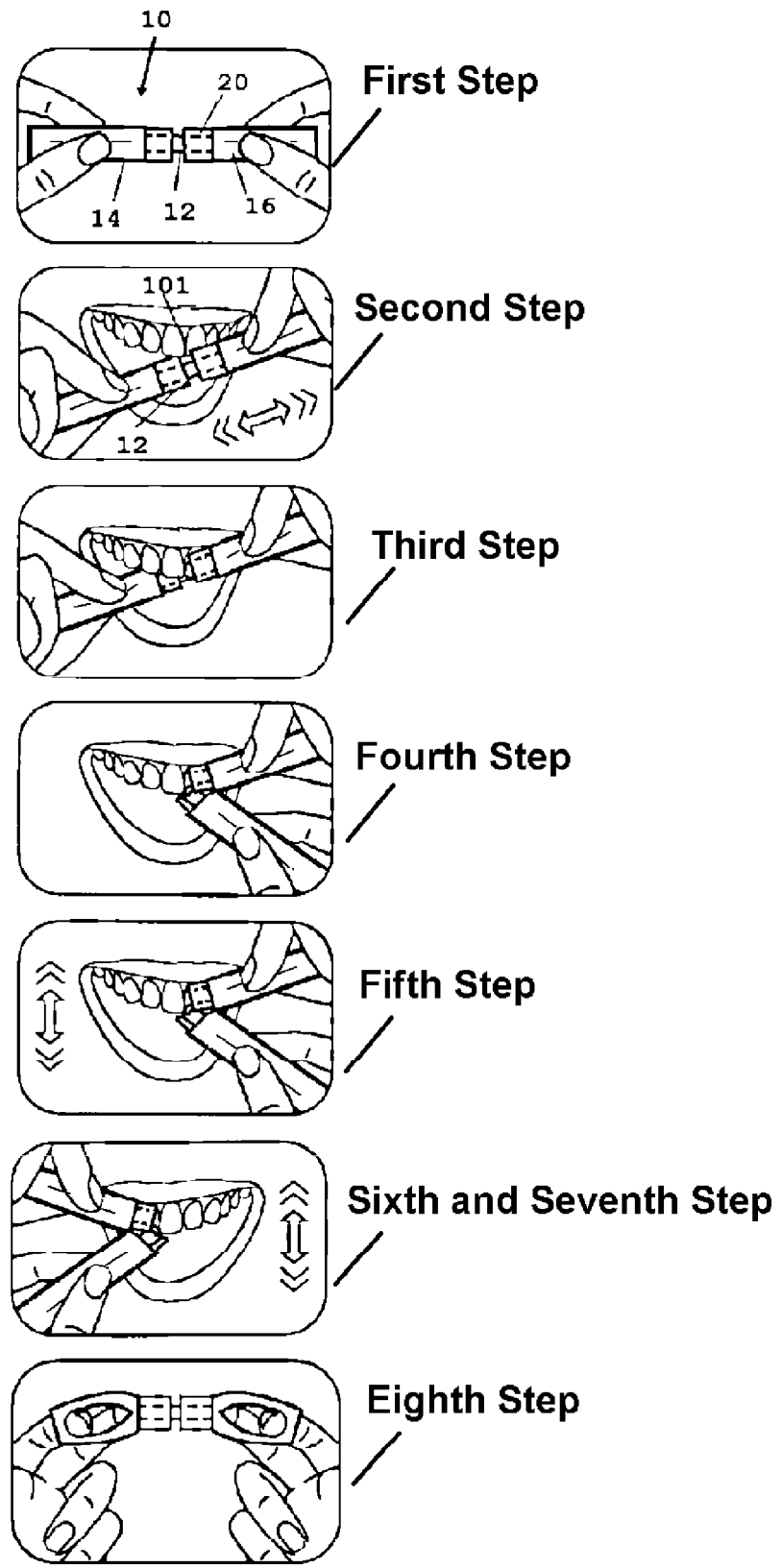
FIG. 17 shows a sequence of eight steps in one preferred mode of employment of the device with the handles engaged between a finger and thumb of opposing hands until the last step wherein slots in the handles are engaged by fingers therethrough.

More detailed depictions of the method of use associated with the device 10 may be seen in FIG. 17. The device 10 is grasped between the thumb a forefinger at the respective handles 14,16. The user then engages the flossing substrate 12 within the engagement zone 22, overlap 24, or abutted edge 26,30 of the edible substrate 20 to glide into the space 101 between two adjacent teeth 100. A flossing up and down motion, or reciprocating motion, then proceeds to cause a cleaning of the space between teeth while saliva upon the saliva coated teeth and/or gums, continually dissolves the edible substrate 20.

These steps are then repeated on the adjacent teeth. Additionally, in the preferred method for cleaning back teeth and other hard to reach teeth, the user engages the forefinger into the slit 70 of the handles 14,16, and then can press the tips of the middle finger against the handles 14,16 creating tension in the device 10 for improved flossing, as is described immediately below.

Figure 17A:
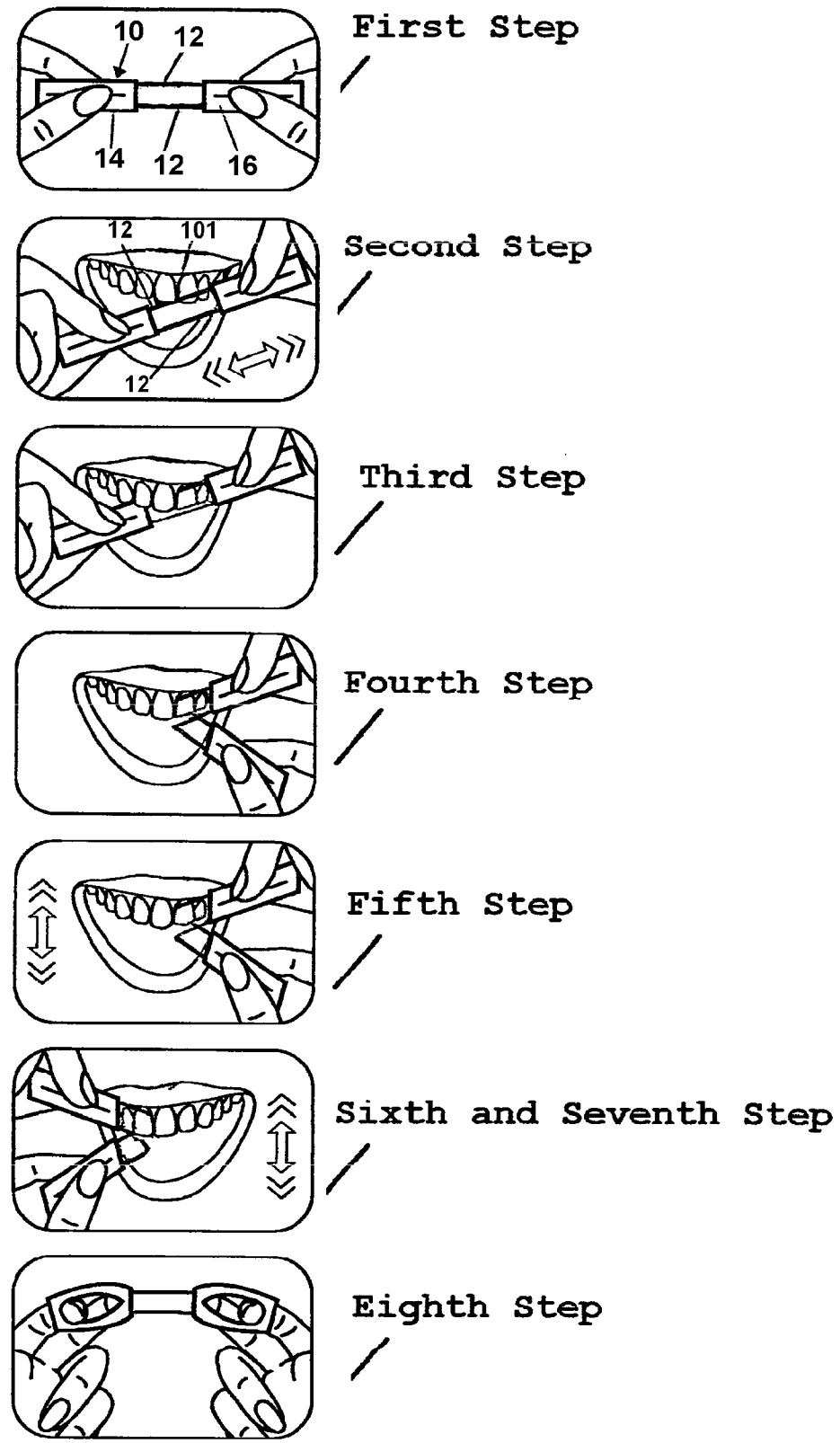
FIG. 17a depicts a sequence for employment of the device similar to that of FIG. 17 but without a dissolvable component using opposing handles engaged between a thumb and a finger of each hand in a first as-used position, and culminating in an eighth step with one finger engaged in a respective slot communicating through each handle.

FIG. 17a depicts steps in employment of the device 10 in a mode with parallel flossing substrates 12 and without the dissolvable component shown in FIG. 17. As shown, the device 10 is grasped between a thumb and forefinger at the respective handles 14,16 whereby the two flossing substrates 12 may be pulled taught. The user then engages one of the two flossing substrates 12 within the glide into the space 101 between two adjacent teeth 100. A flossing up and down motion, or reciprocating motion, then proceeds to cause a cleaning of the space 101 between adjoining teeth. These steps are then repeated on the adjacent pairs of teeth. Additionally, in the preferred method for cleaning back teeth and other hard to reach teeth, the user engages the forefingers into the slits 70 of both handles 14,16, and then can engage one of the two strands of flossing substrate 12 between the spaces 101 between rear pairs of teeth.

Figure 17B:
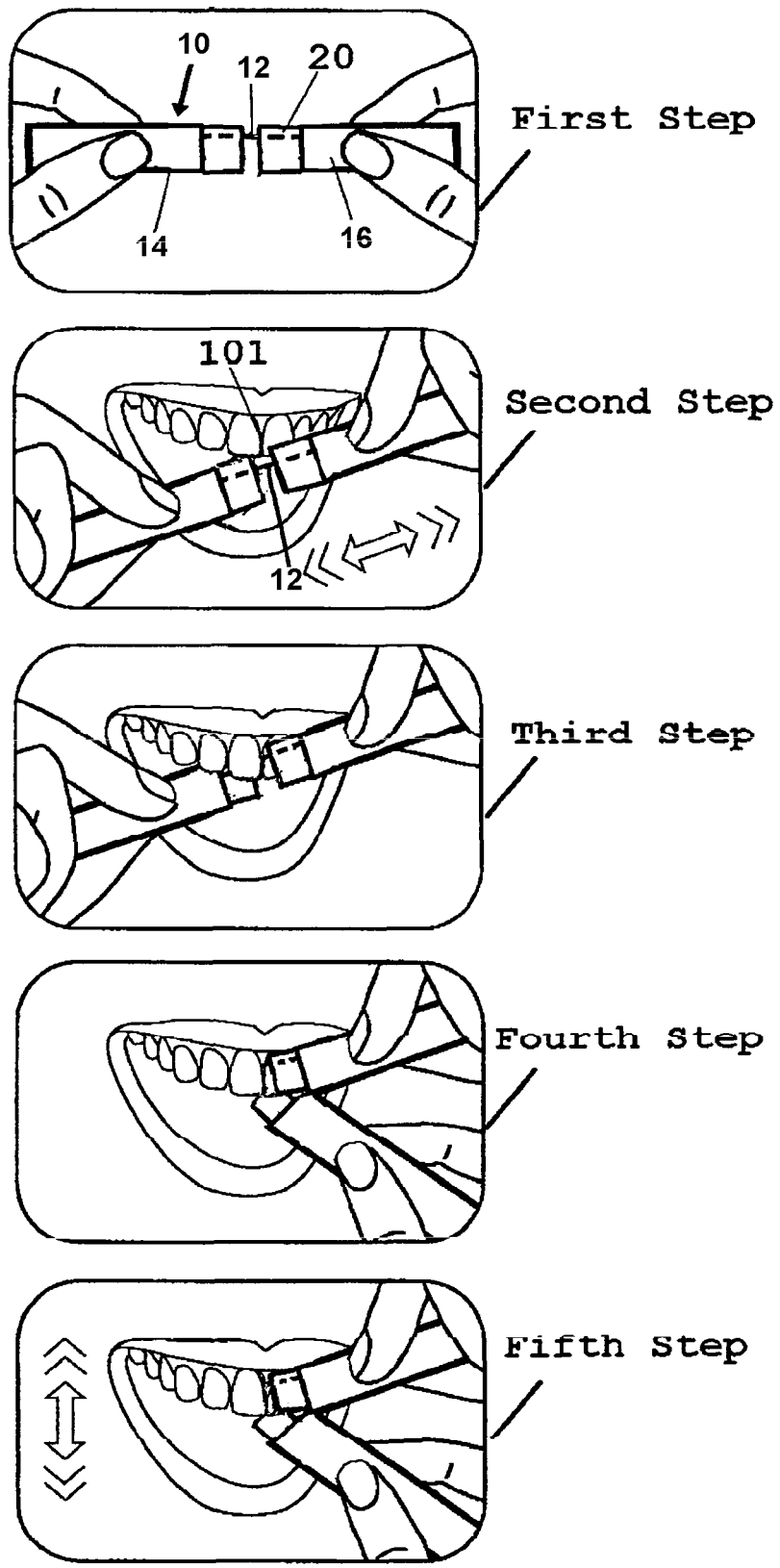
FIG. 17b shows the device in a mode having a single strand of flossing substrate in an offset position between opposing handles with opposing dissolvable components.

In FIG. 17b steps of employment of the device 10 in a mode having a single strand of flossing substrate 12 and opposing dissolvable components provided by an edible substrate 20 adjacent a first handle 14 and second handle 16 is shown with the device 10 in an as-used position. As shown, the single strand of flossing substrate 12 is offset from the center of both handles adjacent one edge of each of the handles 14 and 16. This offset positioning of the single strand of substrate 12 allows the handles to be positioned to more easily slide toward the gums of the user when held in a sandwiched or compressed engagement between the thumb and a finger of each hand. The dissolvable component provided by the depicted edible substrate 20, comes into contact with both sides of the teeth as shown, during use.

FIG. 18a shows a view of the device 10 in the as used mode showing the handle 14 in preferred splayed engagement. This engagement provided by the handles, following the contour of a forefinger of the user, as would be achieved in the first seven steps of the sequence of steps of FIG. 17. The splayed engagement provides a means to prevent slippage of the handle 14 from a finger during use by maintaining an increased surface contact and curved engagement which resists slippage.

FIG. 18b shows, with the mode of FIG. 12a depicted, an alternate, and optional, preferred eighth step that may be substituted for the first step in the sequence of steps of FIG. 17 which may be further optionally modified throughout, as not shown, for use of the device 10. The splay 71 formed following the curve of the user's finger provides a more comfortable and secure engagement thereto. FIG. 18 shows an easy way to hold the device 10 tensed upon or between forefingers and pressed by tips of middle fingers at the ready. Alternately, instead of middle fingers, two thumbs can be used to further maneuver the device 10, where one thumb is not shown in FIG. 18b.

Referring to the first step of the sequence of eight steps for use of the device 10, depicted in FIG. 17, FIG. 18 shows an alternate, and optional, eighth step of the method of use of device 10 from FIG. 12 easily held and tensed by forefingers and pressed by tips of middle fingers at the ready to subsequently, and as not shown, with a forefinger engaged with each longitudinal slit or aperture 70 of each handle 14 and 16 and with the tip of a middle finger with each handle 14 and 16, easily maneuver and use the device 10 to floss behind and between back teeth and/or between front teeth and anything in between.

It is additionally preferred that the slit or aperture 70 be partially or substantially non-tearing slits 70 as the tension imposed on the distal ends of the slits 70 may tend to tear the handles 14, 16. However the degree of tearing can be minimized by employing at least one additional top or bottom layer of the non-stretchable or substantially non-stretchable fabric such as the 3M adhesive cloth tape, Dupont TYVEK spunbonded high density polyethylene, or a nonwoven spun-bonded high density polyethylene fabric adapted to the task herein. It is the above tensioned engagement of fingers with the slits 70 that forms the splay 71 providing a friction enhancing surface for a finger-engagement and resulting comfort when under tension.

Additionally, handle portions 14,16, in all preferred modes of the device 10, may be formed of injection molded polypropylene as opposed to employing the sandwiched engagement of adhesive backed fabric. It is preferred that the injection molded or otherwise formed polypropylene be employed substantially thin, preferably about 0.015 inch (0.038 centimeter), to ensure a comfortable and flexible grip yet still provide a thickness that does not allow the handles 14,16 to break. Further, it is advantageous that the slit 70 alternatively be employed has a slot having a substantial width as to allow a user's forefinger to easily engage within the slot as needed for the as used mode shown previously.

Figure 19:
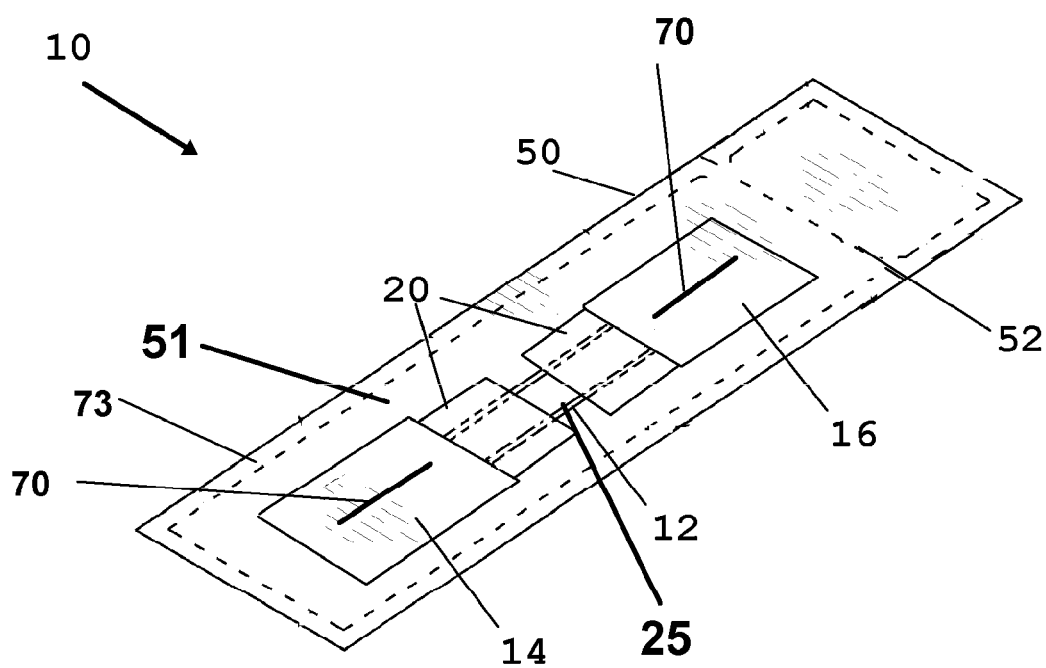
FIG. 19 is a perspective view of the device in a particularly preferred mode, wherein it is surrounded by a removable package forming a clean, substantially sterile, moisture proof storage compartment for storage and transport of the device therein in any mode disclosed.

In FIG. 19 there is shown a perspective view of the device 10 in another particularly preferred mode which would be employable in a portable but clean, moisture proof fashion. This mode of the device 10 would be particularly adapted for being carried by the user during travel, or for dispensing by hotels and the like to patrons staying on the property much like soap and other toiletries.

As depicted, the device 10, which could be any mode of the device 10 described herein is surrounded by a removable package 50 forming a clean, moisture proof storage compartment 51 for the device 10 therein. The package 50 is shown in transparent form, however it can also be opaque and may have indicia thereon showing the name of the hotel or dispensing entity. Further, the indicia may also include the depicted steps of FIG. 17 to educate users as to the proper manner to employ the device 10 once removed from the package 50.

In the mode of the device 10 in combination with the package 50 of FIG. 19, the device 10 is generally employed in a single use disposable manner. In a method of use, the user would hold the device 10 encased within the clean, substantially moisture proof compartment 51 of the package 50 in their hands. In a next step, a frangible or tear off portion 52 would be removed to provide a means to access the device 10 within compartment 51 of the package 50. The compartment 51 may have a release liner 73 to prevent the device from sticking to the sidewalls of the compartment 51 such as a film of non-stick plastic material. Once the tear off portion 52 is removed the device 10 would be extracted and the user would employ the device 10 in the method of steps depicted in FIG. 17. Once finished the user would dispose of the device 10 and the package 50.

Such individual combinations of the device 10 and package 50 may be sold separately or in a container of many individual packages 50 which may be separated or may be on a roll of individually removable packages 50 with each containing a device 10 within their respective compartment 51. Sold and distributed in bulk, the device 10 would be especially adapted for use and individually dispensing, or sampling, to any global or domestic manufacturer or marketer of pre-existing globally branded or retail-store branded dental flosses, trade show booths and dental schools for dentists or dental hygienists, dental patients visiting the dentist or dental hygienist, medical patients visiting a medical doctor or dentist who prescribes regular flossing to minimize system-wide inflammation due to gum disease, guests in their hotel bathrooms, first class airline passengers, cruise ship passengers in their cabin bathrooms, astronauts, hospital patients, crew members in submarine bathrooms, elementary school teachers and/or elementary school students in their classrooms, women on the go carrying purses, men whose clothes have pockets, oral care companies and/or insurance companies who analogous to providing good driver discounts or discounts for exercise and/or prevention seek better compliance by dental patients monitored by dental or medical professionals, and other venues such as travel kits or inserts to or piggybacked on boxes of a global brand of toothpaste on the shelves of supermarket aisles where users may not yet have their own supply of floss with them, or where a one-use flossing component, or likeness of such a component and proper flossing instructions actually purchased in a virtual world created by residents (people like you) participating on the world wide web in games simulating real life such as the Second Life® game by Linden Research Inc. whose well known on-line games can also be a virtual way to encourage or train someone on a new flossing component virtually before they attempt the real thing in real life, would all be especially desirable when used for the first time or used regularly to help maintain, improve or help encourage the habit of improving oral health and system-wide health.

Figure 20A:
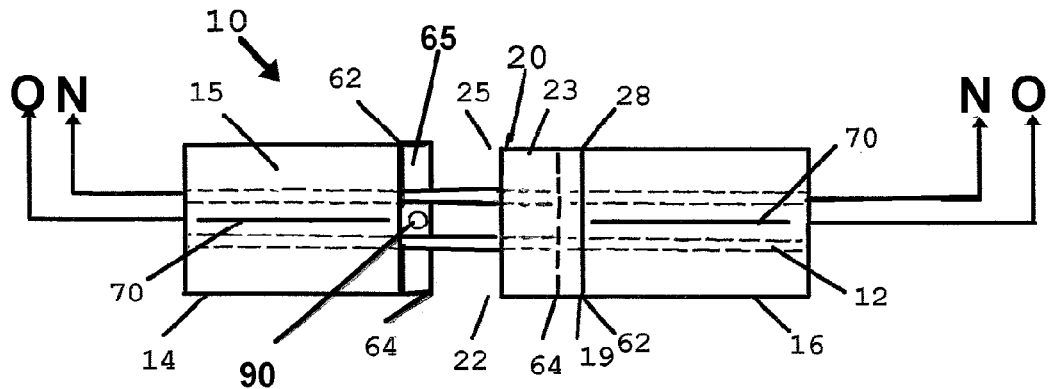
FIG. 20a depicts an additional preferred mode of the device showing a top plan view with a dissolvable component formed as a layer of edible substrate extending from one handle and a dissolvable capsule engaged on a substantially central portion on the other, the capsule preferably being a breath freshening capsule.
Figure 20B:
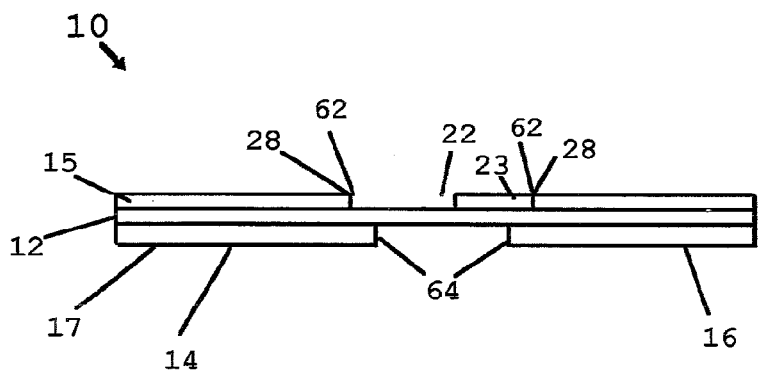
Figure 20C:
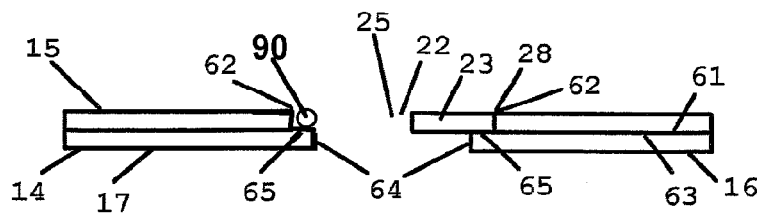

An additional preferred mode of the device 10 is shown in FIGS. 20*a*, 20*b*, and 20*c*. Similar to other modes of the device 10 shown in previous figures, the first or top planar portion 15 has, as shown in FIG. 20*c*, an inner most surface 61 and the second or bottom planar portion 17 has an inner most surface 63. As is preferred in the current mode, and further evidenced in FIG. 20*c*, and therein the second handle 16, a portion 23 of edible substrate 20 is engaged on a ledge or an inner most portion 65 of the inner most surface 63 of the second or bottom planar portion 17 thereof, thereby joining the portions 23 of edible substrate 20 to the handle 16. Alternatively, on the first handle 14 there is clearly seen a dissolvable component in the form of capsule 90 engaged in a substantially central position on the ledge or an inner most portion 65 of the inner most surface 63 of the second or bottom planar portion 17 of the handle 14 thereby joining the capsule 90 to the handle 14, shown clearly in FIGS. 20*a*, 20*c* and 20*d*. Additional preferred means for engaging the capsule are shown later in FIGS. 21-23.

As even further evidenced in FIGS. 20*a* and 20*c*, the dissolvable capsule 90 and portion 23 of edible substrate 20 are engaged respectively on the handles or ledge or inner most portion 65 of each handle 14 and 16 at or near the inner most edges 62 of the first or top planar portion 15 of the handles 14 and 16 at the respective abutted edges 28 shared therebetween. Again, as in the device of FIG. 1, a gap 25 defining a means for targeting or an engagement zone 22 is formed in a centrally located position on the device 10 providing the target for means of engagement of the device 10 for use.

It is noted that the employment of the dissolvable capsule 90, similar to that of the substrate 20, is intended to elicit a pleasant gustatory and/or olfactory sensation in the user during the use of dental floss device 10 in a proper fashion, that is, the user's saliva tends to wet the handles during use and therefor additionally wet and dissolve the dissolvable capsule 90 and substrate 20. In accordance to at least one preferred mode of the device 10 the most favored dissolvable capsule 90 is one provided by the patent to Mane et al (U.S. Pat. Nos. 7,754,239 and 7,744,922), herein incorporated in their entirety by reference, teaching fast dissolving (and filled) dissolvable capsules employing some gelatin (and sorbitol) in the shell of the capsule having a breath freshening core. There is further noted a non-gelatin capsule shell formation found in U.S. Pat. No. 6,949,256 issued to Fonkwe et al, herein incorporated in its entirety by reference, whose abstract indicates that the non-gelatin capsule shell is intended "for encapsulating wet or dry materials including medicinal dosage forms, nutritional supplements . . . etc."

Still further, it is noted that in accordance with all modes of the device employing a dissolvable component provided by one or a plurality of dissolvable capsules, it is to be understood that the dissolvable capsule is not limited to the favored elements described above, however can be any one from a group including candies and mints such as ALTOIDS, M&M'S, TIC-TACS, THERAMINTS, other commercially and non-commercially available mints. As such, the dissolvable component can be formed one or a combination of wet or dry ingredients from a group of ingredients including, a dissolvable component formed as a solid solution such as dissolvable candies and mints, or a dissolvable capsule containing a core formed of one or a combination of wet or dry materials from a group including, a breath freshening core, a medicinal dosage, nutritional supplements, flavoring, mouthwash, a cooling agent, a heating agent, a dental plaque disclosing agent, a medicine and nutritional supplements.

An additional note is made that the flossing substrate 12 can be formed from a thermoplastic elastomer (TPE) which can be an elastic polyether block amide, known commonly under the trademark Pebax (available from Arkema). Alternately, the flossing substrate 12 can be formed from an inelastic ePTFE such that the aperture 40 can be laser cut to form the flossing substrate 12. The flossing substrate 12 thus can be formed in this mode, as one skilled in the art will appreciate, out of elastic or inelastic material. Alternately, in accordance with this preferred mode of device 10 the composition of another favored flossing substrate 12 is provided by the patent(s) to Chen (U.S. Pat. Nos. 5,153,254 and 6,161,555), herein incorporated in their entirety by reference, teaching a gelatinous elastomer composition, or crystal gel, that can be shaped or formed, for example by molding or casting, into the flossing substrate 12 of device 10 of FIGS. 29a and 29b (and FIGS. 10a and 10b, and FIGS. 11a and 11b, and FIGS. 14a and 14b). As indicated by Chen, such a gelatinous elastomer composition, or crystal gel, shaped into a floss removes dental plaque from between teeth at the same time that the gelatinous elastomer composition, or crystal gel is gentle on the gums. Such a preferred gelatinous elastomer composition, or crystal gel, formed into the flossing substrate 12 of device 10, is not only much more gentle on gums than any regular string floss employing, for example, an elastic polyether block amide (such as the string of Johnson & Johnson's elastic "REACH" "TOTAL CARE" dental floss tape or inelastic ePTFE (such as the string of Procter & Gamble's ePTFE "GLIDE" dental floss tape), but compared to any string floss, device 10 is also much easier, much more comfortable and breath freshening.

Still further, it is noted that the handles 14, 16 of the currently disclosed preferred mode of the device 10, as well as all other modes of the device 10, may be entirely formed of, or have top and bottom planar portions 15, 17 formed of one or a combination of handle materials from a group including, flexible nonwoven fabric; woven fabric; woven rayon acetate tape; spunbonded polypropylene nonwoven fabric; spunbonded nylon nonwoven fabric; spunbonded blended polyolefin hydrophobic nonwoven fabric; high density polyethylene nonwoven fabric; powder-free, scent-free, latex-free rubber; thermoplastic elastomer polyether block amide; thermoplastic elastomer; spunbonded polypropylene hydrophobic nonwoven fabric; laser cut woven or nonwoven fabric; and other suitable materials.

Further, it is preferred that a transfer adhesive is employed in order to engage the top and bottom portions 15, 17 forming the handles 14, 16 such as a hypoallergenic medical grade transfer adhesive (available as product #1524 from 3M). An alternate to a transfer adhesive is a hotmelt adhesive (available as product #H20009 from Bostik or, as most preferred, product #H2465 from Bostik). A further note is made in that the flossing substrate 12 can be formed from an elastic thermoplastic elastomer polyether block amide such as that employed in Johnson & Johnson's "REACH" "TOTAL CARE" dental floss tape, which is elastic.

Figure 20D:
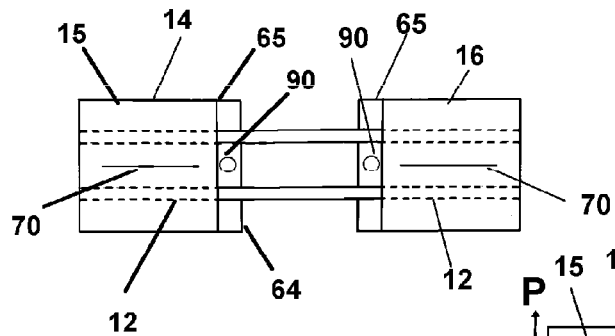
FIG. 20d shows a view of another preferred mode of the device showing first and second handles each employing a capsule in a preferred engaged position on the ledge portion.

FIG. 20d shows another preferred mode of the device 10 wherein the first and second handles 14, 16 each employ dissolvable capsules 90 in a substantially mirrored configuration. As is shown, it is to be understood that the longitudinally spaced apart capsules 90 from one handle 14 to the other 16 in such a mode can have the general appearance to the user as a whole, especially to young children and football fans and other adults, to resemble longitudinally spaced apart small "goal posts". Therefore the capsule 90 'goal posts' provide a physical target to identify the engagement zone 22 and therefore assist the user to maneuver through the space or gap 25 during use.

In use, as the user successfully passes the flossing substrate 12 between two adjacent incisors 100, the 'goal posts' are contacted essentially telling the user they have reached the 'goal'. At the same time the 'goal posts' of the dissolvable capsule 90 are dissolved in the warm and moist environment of the mouth upon contact with saliva. The dissolving capsule 90 thereby releases the breath freshening or other core during flossing, and thereby conveys that the user has 'scored' the requisite 'points'. The user can readily perceive the gustatory and/or olfactory rewards at the same time the user is eyeing the gap 25 and flossing substrate 12 of device 10 for cleaning/flossing between teeth for 'scoring' essentially multiple 'points' of the instant floss invention, which is use-reinforcing for users.

Figure 21A:
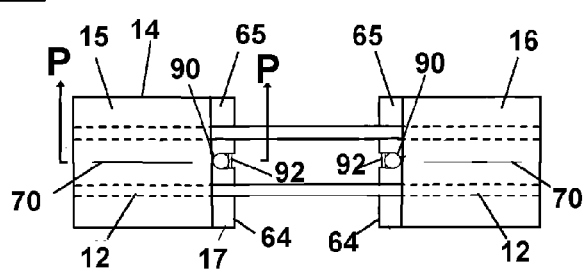
FIG. 21a shows a view of another preferred mode of device showing the first and second handles each employing capsules in another preferred engaged position on the ledge portion employing partial circumferential engagement with a tab portion.
Figure 21B:
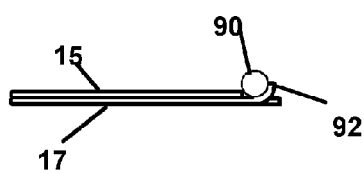

In FIG. 21a and FIG. 21b, there is an additional preferred mode of the device 10 wherein both handles 14, 16 employ dissolvable capsules 90 in a substantially mirrored configuration with the dissolvable capsule 90 engaged to the ledge portions 65 of the handles 14, 16. The capsule 90 is positioned substantially central on the ledge or an innermost portion 65 and an additional tab portion 92 of the bottom planar portion 17 near the inner most edge 64 is employed for engagement about a substantial surface area of the capsule 90, providing secured engagement thereon.

Figure 21C:
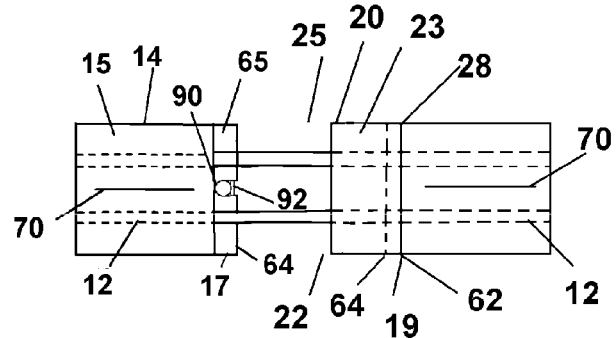
FIG. 21c depicts an additional preferred mode of the device having a dissolvable capsule engaged on the first handle in accordance with the mode of FIG. 21a, and layer of edible substrate engaged to the second handle and extending therefrom.

FIG. 21c shows yet another preferred mode of the device 10 wherein the second handle 16 includes a portion 23 of edible substrate 20 engaged on a ledge or an inner most portion 65 of the second or bottom planar portion 17 thereof, thereby joining the portions 23 of edible substrate 20 to the handle 16. The first handle 14 includes a dissolvable capsule 90 engaged substantially central on the ledge or an innermost portion 65 in a manner similar to that of FIG. 21a. As can be seen the additional tab portion 92 of the bottom planar portion 17 near the inner most edge 64 is employed for engagement about a substantial surface area of the capsule 90, providing secured engagement of the capsule 90 to the first handle 14.

Figure 22A:
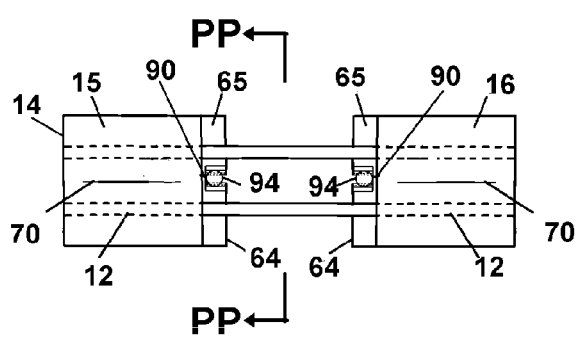
FIG. 22a shows a view of another preferred mode of device showing the first and second handles each employing a capsule in a yet another preferred engaged position on the ledge portion employing a longitudinal slit such that the capsules are essentially cradled within the slits.
Figure 22B:
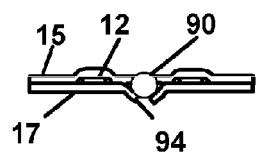

In FIG. 22a and FIG. 22b there is yet an additional preferred mode of the devices employing other means for engaging the capsule 90 to the ledge or innermost portion 65. As can be seen there is a longitudinal slit 94 extending from the inner most edge 64 of the bottom planar portion 17 such as to provide a kind of cradle to nestle or otherwise engage the capsule 90 about a larger surface area.

Figure 22C:
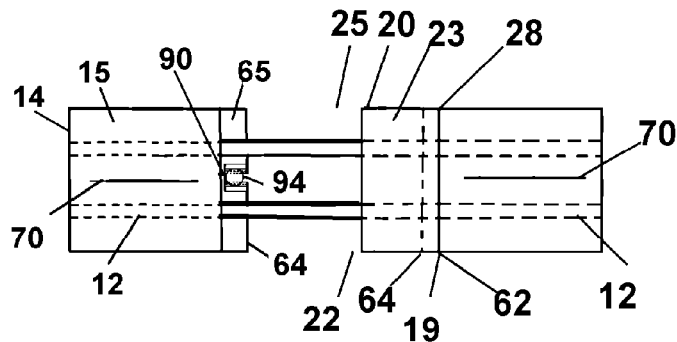
FIG. 22c depicts an additional preferred mode of the device having a dissolvable capsule engaged on the first handle in accordance with the mode of FIG. 22a, and a layer of edible substrate engaged to the second handle and extending therefrom.

FIG. 22c shows still yet another preferred mode of the device 10 wherein the second handle 16 includes a portion 23 of edible substrate 20 engaged on a ledge or an inner most portion 65 of the second or bottom planar portion 17 thereof, thereby joining the portions 23 of edible substrate 20 to the handle 16. The first handle 14 includes a dissolvable capsule 90 engaged substantially central on the ledge or an innermost portion 65 in a manner similar to that of FIG. 22a. As can be seen, a longitudinal slit 94 extending from the inner most edge 64 of the bottom planar portion 17 provides a kind of cradle to nestle or otherwise engage the capsule 90 about a larger surface area providing secured engagement of the capsule 90 to the first handle 14.

Figure 23A:
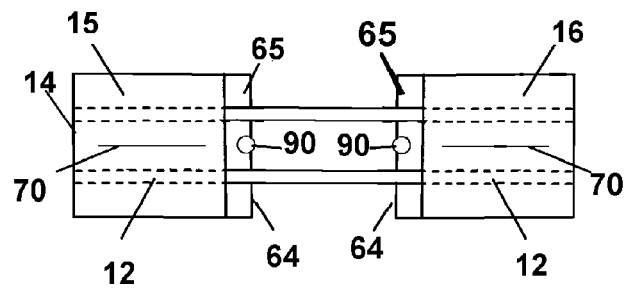
FIG. 23a shows a view of another preferred mode of device showing the first and second handles each employing a capsule in yet another preferred engaged position on the ledge portion disposed at or near the innermost edge of the handle.

Further, in FIG. 23a there is still another preferred mode of the device 10 showing another preferred engaged position of the capsule 90 to the respective handles 14, 16. As shown, the capsules 90 shown are engaged on the ledge or innermost portion 65 in a position extending substantially past the inner most edge 64 of the bottom planar portion 17. This mode ensures the user's saliva will contact the capsules 90, 91 almost immediately when employed properly.

Figure 23B:
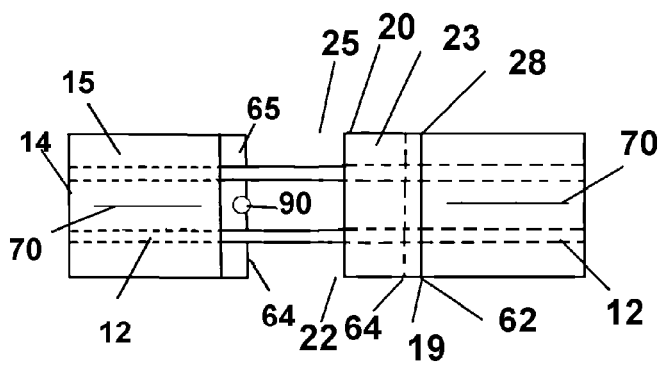
FIG. 23b depicts an additional preferred mode of the device having a dissolvable capsule engaged on the first handle in accordance with the mode of FIG. 23a, and a layer of edible substrate engaged to the second handle and extending therefrom.

FIG. 23b shows still another preferred mode of the device 10 wherein the second handle 16 again includes a portion 23 of edible substrate 20 engaged on a ledge or an inner most portion 65 of the second or bottom planar portion 17 thereof, thereby joining the portions 23 of edible substrate 20 to the handle 16. The first handle 14 includes a dissolvable capsule 90 engaged substantially central on the ledge or an innermost portion 65 in a manner similar to that of FIG. 23a. As can be seen, the capsule 90 is engaged on the ledge or innermost portion 65 in a position extending substantially past the inner most edge 64 of the bottom planar portion 17.

Figure 24A:
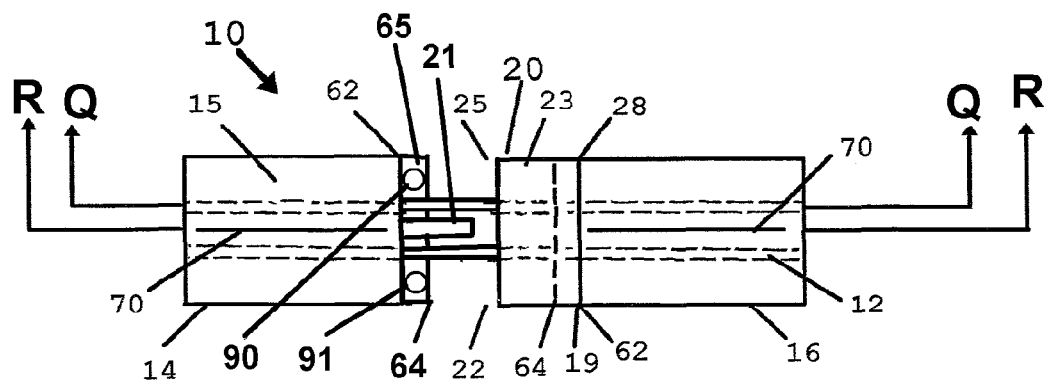
FIG. 24a depicts an additional preferred mode of the device showing a top plan view with the dissolvable component provided by a layer of edible substrate extending from one handle, and at least two dissolvable capsules and a strip of edible substrate engaged on the other handle, again the capsules are preferably a breath freshening capsule.
Figure 24B:
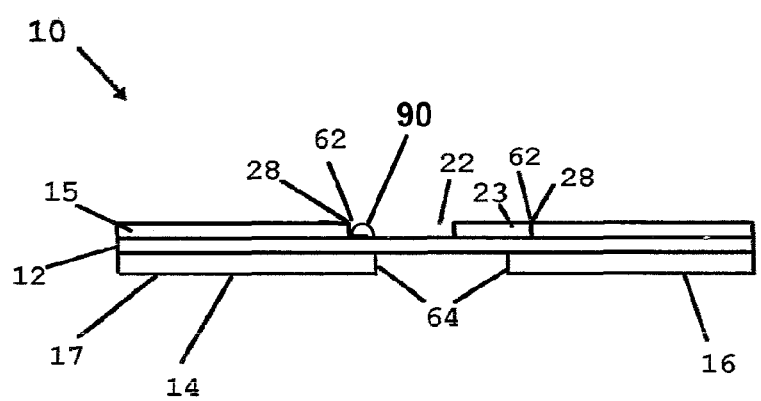
Figure 24C:
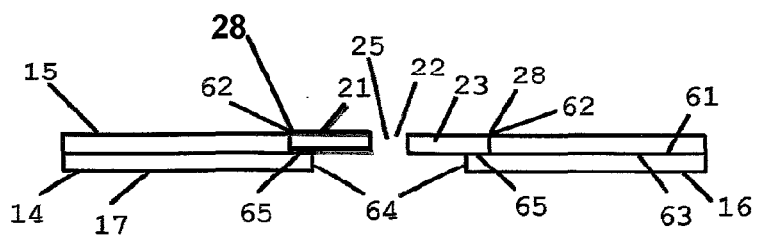

A still further additional preferred mode of the device 10 is shown in FIGS. 24a, 24b, and 24c. In this mode, on the first handle 14 there is clearly seen a first dissolvable capsule 90 and a second dissolvable capsule 91 spaced a distance apart and engaged at or near the corners of the ledge or an inner most portion 65 of the inner most surface 63 of the second or bottom planar portion 17 of the handle 14 thereby joining the capsules 90, 91 to the handle 14. Additional preferred means for engaging the capsules 90, 91 to the ledge or innermost portion 65 are shown later in FIGS. 26-28.

Shown and preferred, there is a first portion 21 of substrate 20 engaged to ledge or innermost portion 65 and disposed substantially midway between the capsules 90, 91. As could be imagined, the device 10 in the current mode provides a gustatory and/or olfactory sensation in the user during proper employment.

It is to be noted that it is within the scope of the invention that other modes of the device 10, however not shown, may provide a first handle 14 as shown in previous FIG. 24a, and a second handle 16, being of a substantially mirrored configuration.

Figure 25A:
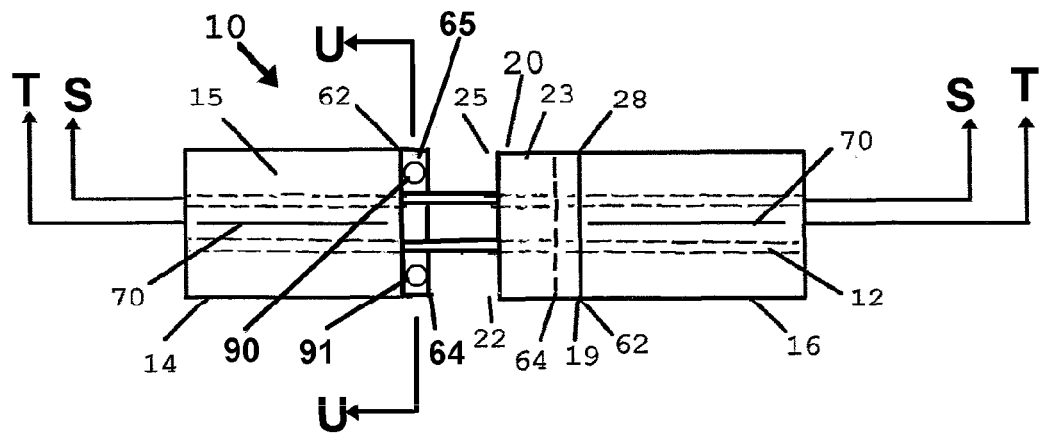
FIG. 25a depicts another preferred mode of the device showing a top plan view with dissolvable components provided by a layer of edible substrate extending from one handle and at least two dissolvable capsules engaged on the other handle.
Figure 25B:
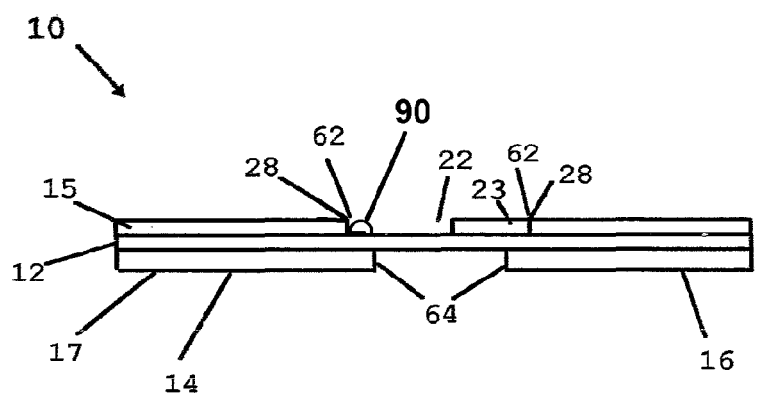
Figure 25C:
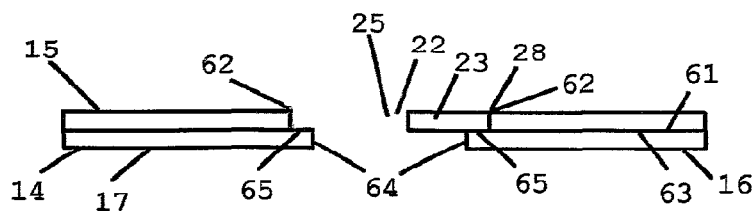
Figure 25D:
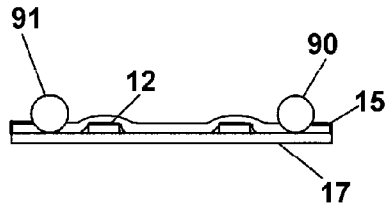

FIGS. 25a, 25b, and 25c show yet an additional preferred mode of the device 10. In the current mode, a first and second capsule 90, 91 are provided, similar to that in FIGS. 24a-c, however in this mode no portion 21 of substrate 20 is provided. As such, a gustatory and/or olfactory sensation will still be provided. A partial end view of the first handle 14 is shown in FIG. 25d.

Figure 26:
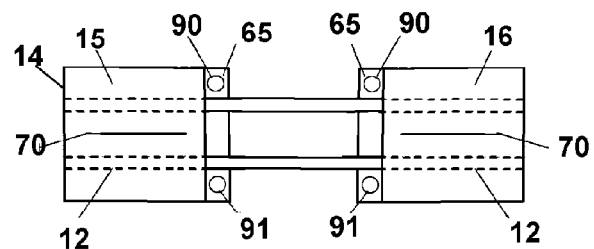
FIG. 26 shows a view of another preferred mode of device showing the first and second handles each employing first and second capsules in a first preferred engaged position on the ledge portion.

FIG. 26 shows still another preferred mode of the device 10 wherein the second handle 16 also employs a plurality of dissolvable capsules 90, 91 in a substantially mirrored configuration to the first handle 14.

Figure 27A:
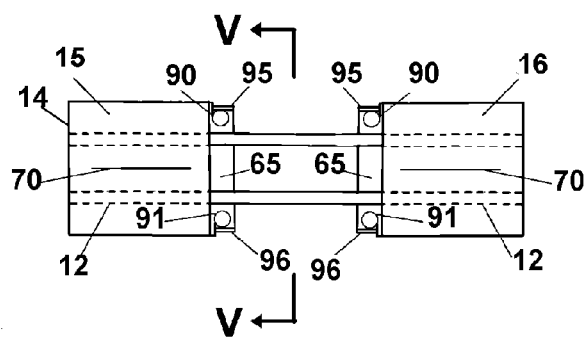
FIG. 27a shows a view of another preferred mode of device showing the first and second handles each employing first and second capsules in another preferred engaged position employing partial circumferential engagement with respective transverse tab portions.
Figure 27B:
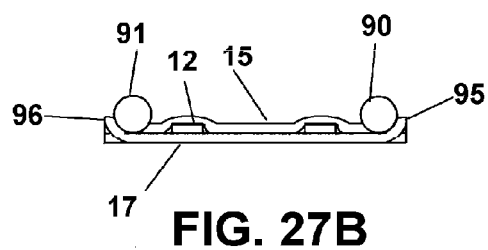

FIG. 27a shows a view of yet another preferred mode of the device 10 the handles 14, 16 in a substantially mirrored configuration employing an additional preferred means for engaging first and second dissolvable capsules 90, 91 thereon. In this mode, the capsules 90, 91 are similarly spaced a distance apart and engaged at or near the corners of the ledge or an inner most portion 65 wherein first and second transverse tab portions 95, 96 are operatively employed for substantial surface area engagement with the capsules 90, 91. As shown in the partial end view of FIG. 27b, it can be clearly seen that the engagement of the transverse tab portions 95, 96 about the surface area of the capsules 90, 91 provide added secured engagement over the simple planar engagement shown in the previous mode.

Figure 28:
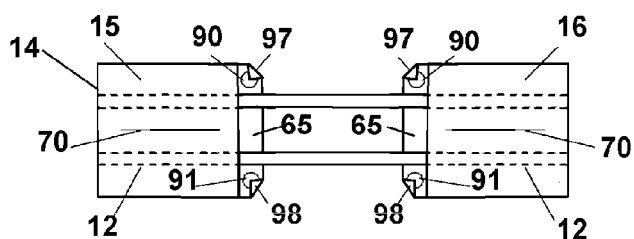
FIG. 28 shows a view of another preferred mode of device showing the first and second handles each employing first and second capsules in yet another preferred engaged position employing partial circumferential engagement with respective corner tab portions.

FIG. 28 shows a view of yet another preferred mode of the device 10 with the handles 14, 16 employing yet another preferred means for engaging the first and second dissolvable capsules 90, 91. As is shown, the capsules 90, 91 are similarly spaced a distance apart and engaged at or near the corners of the ledge or an inner most portion 65 wherein the corners 97, 98 are folded over providing surface area engagement with the capsules 90, 91.

Further, it is noted that in other modes of the device 10 not shown yet readily recognized by one skilled in the art that the device 10 may include a first handle 14 employing first and second capsules 90, 91 similar to that of FIG. 27a or 28 in combination with a second handle 16 employing edible substrate 20 engaged at or near the second handle 16. In these modes, the dissolvable component or edible substrate 20 may be engaged in accordance with any of the disclosed means to engage the substrate 20 thereon, and are anticipated.

Figure 29A:
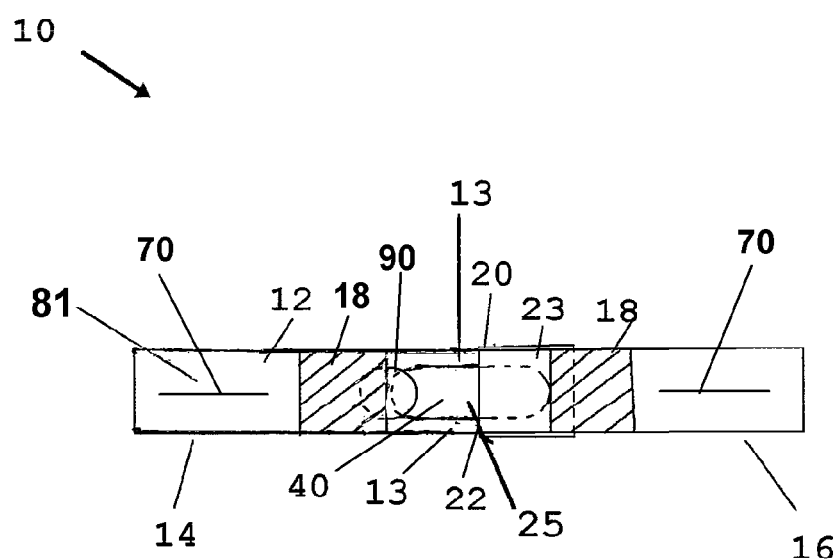
FIG. 29a shows another mode of the device having a slit or aperture formed to communicate through the handles, employing a combination of dissolvable components provided by an edible substrate on one handle and a dissolvable capsule engaged on the other handle.
Figure 29B:
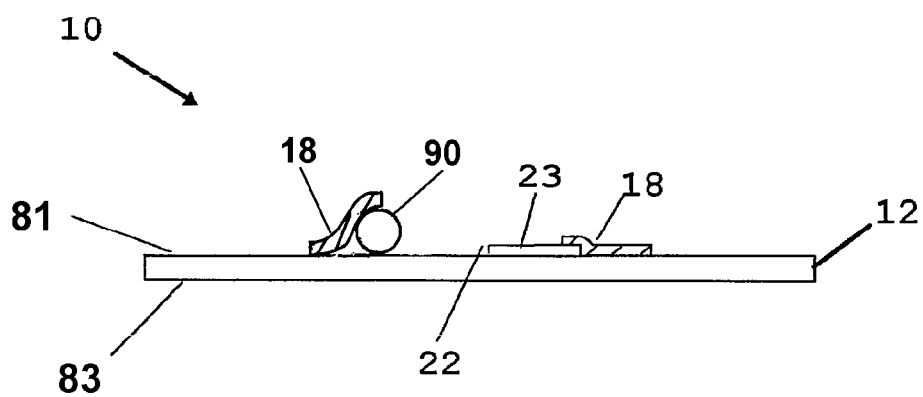

A still further embodiment of a particularly preferred mode of the device 10 is depicted in FIGS. 29a and 29b. First and second handles 14,16 are defined by end portions of the planar flossing substrate 12. Side portions 13 of the planar flossing substrate 12 extend around the perimeter of, and help define the aperture 40, and preferably align with the edge of the adjacent substrate 12 thereby providing an elongated means to floss when engaged within the crevices between teeth.

First dissolvable capsule 90 and second portion 23 of edible substrate 20 are engaged on one surface such as the first or top planar surface 81 of the device by operative means of engagement. Engaged to the flossing substrate 12, the portion 23 is cut or formed in a manner to overlap the aperture 40 and have the same side edge, that is width, as the flossing substrate 12, while the capsule 90 preferably has the same width as the aperture 40. The capsule 90 and portion 23 are engaged at or near the ends of the aperture 40 using means of engagement such as adhesive or tape 18. The portion 23 and capsule 90 extend inward and over the aperture 40. The gap 25 is maintained between the two portions and defines the target for the user in the engagement zone 22 as previously described.

It is once again noted that it is within the scope of the invention that still other modes of the device 10, not shown however readily recognized by one skilled in the art, may provide a first handle 14 as shown in previous FIG. 29a, and a second handle 16, being of a substantially mirrored configuration, and is anticipated.

Figure 30:
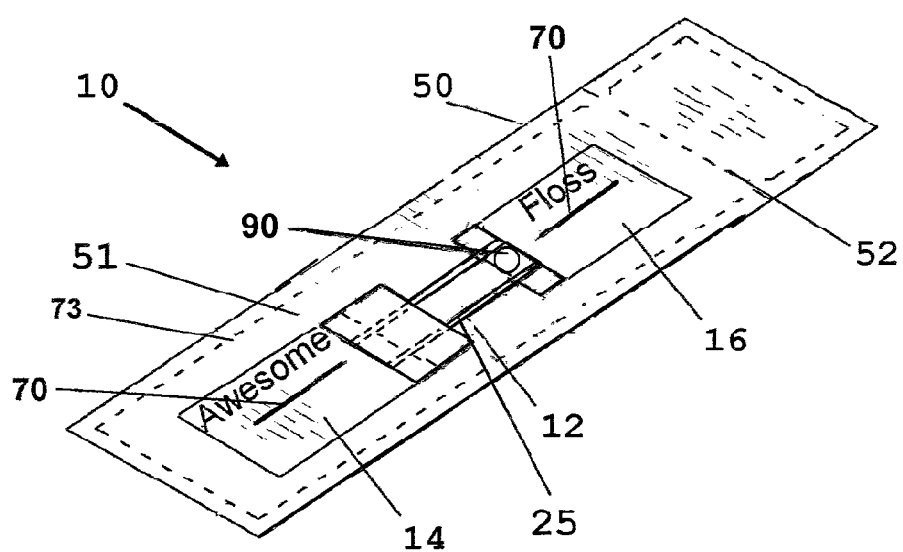
FIG. 30 is a perspective view of the device in a particularly preferred mode, wherein it is surrounded by a removable package forming a clean, moisture proof storage compartment for the device therein.

In FIG. 30 there is shown a perspective view of the device 10 in still another particularly preferred mode which would be employable in a portable but clean, moisture proof fashion, similar to that of FIG. 19 shown previously. This mode of the device 10 would be particularly adapted for being carried by the user during travel, or for dispensing by hotels and the like to patrons staying on the property much like soap and other toiletries.

As depicted, the device 10, preferably being a mode of the device 10 employing a dissolvable component in the form of a dissolvable capsule 90 described herein is surrounded by a removable package 50 forming a clean, moisture proof storage compartment 51 for the device 10 therein. The package 50 is shown in transparent form, however it can also be opaque and may have indicia thereon showing the name of the hotel or dispensing entity. Further, in accordance with modes of the device 10 employing dissolvable components such as film or one or more dissolvable capsules, the package 50 is preferably formed as a kind of rigid blister package, in order to protect the capsule and prevent damage. In use the entire package 50 may be formed as a blister package or, alternatively, only the portion covering the capsule may be of a blister package type. Again, a frangible or tear off portion 52 and a release liner 73 are provided.

Figure 31:
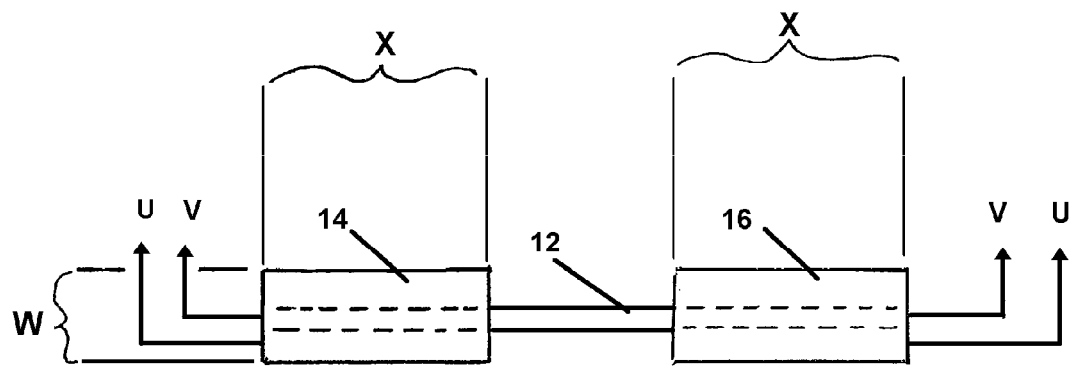
FIG. 31 depicts an additional preferred mode of the device in a plan view showing a single strand of flossing substrate extending between an engagement with two handles.

FIG. 31 depicts a preferred mode of the device 10 showing a top plan view. A single strand of flossing substrate 12 extending between an engagement with a first handle 14 and second handle 16. The flossing substrate 12 as shown in dotted line, extends substantially the entire length of both the first handle 14 and second handle 16 in an engagement therewith.

Figure 32:
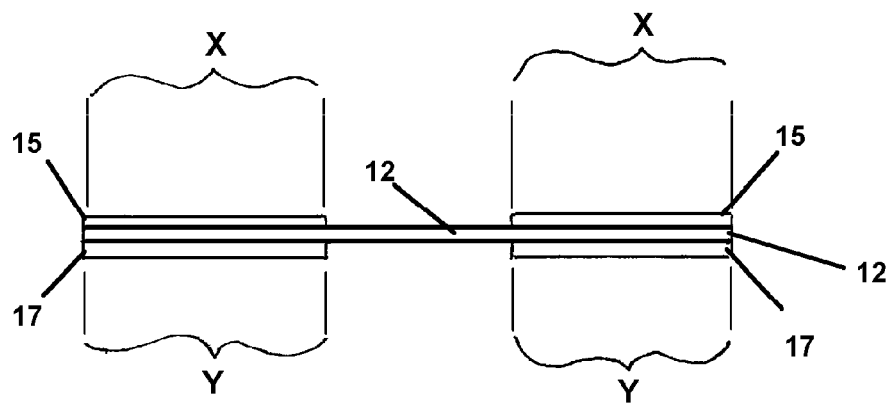
FIG. 32 shows a cross-sectional view of the device of FIG. 31 along line V-V.

As shown in FIG. 32 a cross-sectional view of the device 10 of FIG. 31 along line V-V, the flossing substrate 12 is in a sandwiched engagement between first planar portions 15 and second planar portions 17 of both the first handle 14 and second handle 16 for substantially the entire length "X" of each handle.

Figure 33:
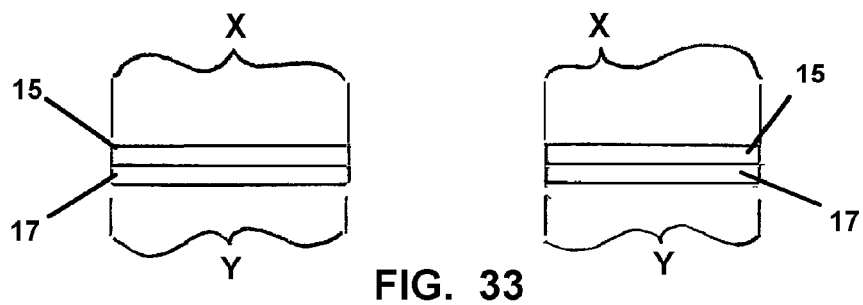
FIG. 33 shows a cross-sectional view of the device of FIG. 31 along line U-U.

As can be seen in FIG. 33 which is a cross-sectional view of the device 10 of FIG. 31 along line U-U, the first planar portion 15 is directly engaged to the second planar portion 17 of both the first handle 14 and second handle 16 in areas where the flossing substrate 12 is not in a sandwiched engagement therebetween.

Figure 34:
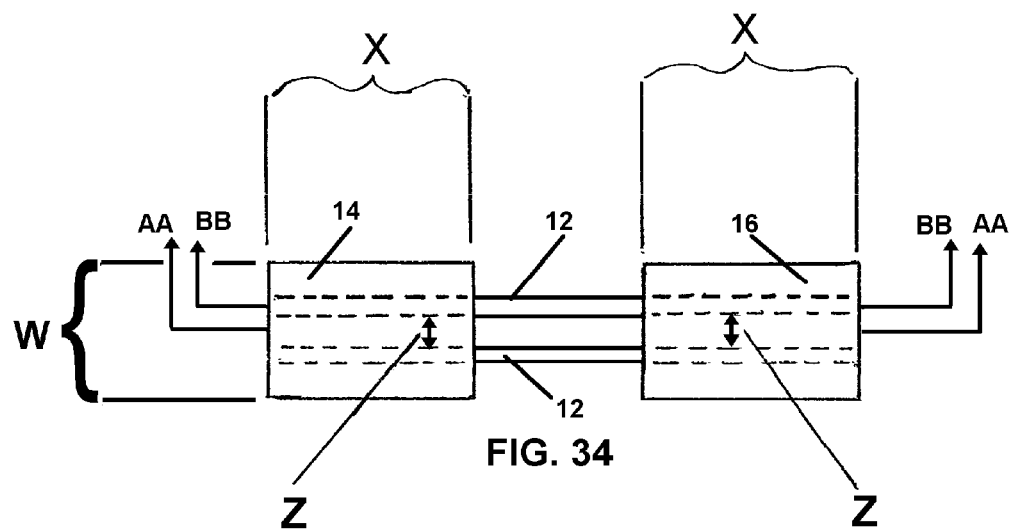
FIG. 34 depicts an additional preferred mode of the device in a plan view showing two strands of flossing substrate extending between respective engagements with two handles.

In FIG. 34 there is shown an additional preferred mode of the device 10 in a plan view, showing two strands of flossing substrate 12 extending between an engagement with a first handle 14 and second handle 16. As can be seen in dotted line, both strands of flossing substrate 12 extend in that engagement across substantially the entire length "X" of both handles and have a separation distance "Z" between their parallel paths.

Figure 35:
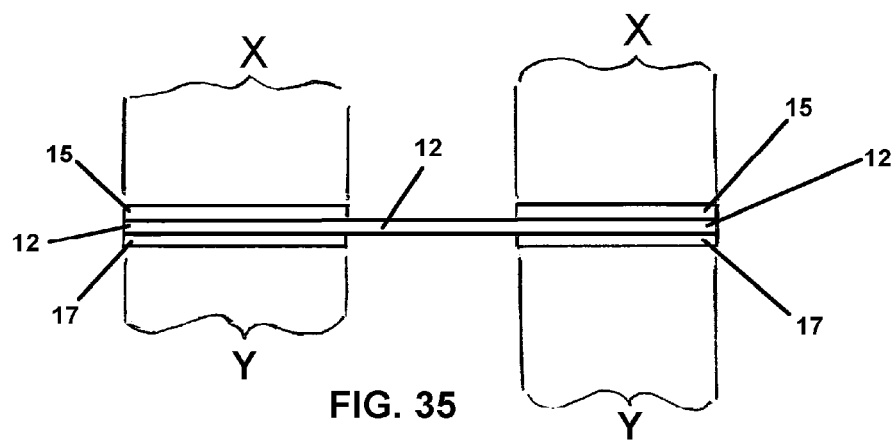
FIG. 35 shows a cross-sectional view of the device of FIG. 34 along line BB-BB.

FIG. 35 depicts a cross-sectional view of the device 10 of FIG. 34 along line BB-BB. As can be discerned from the drawing, the flossing substrate 12 is in a sandwiched engagement between first planar portions 15 and second planar portions 17 of both the first handle 14 and second handle 16 for substantially the entire length "X" of each handle. Experimentation has shown that this engagement running the length "X" of both handles, between the first planar portion 15 and second planar portion 17 in their adhesive engagement, provides an exceptionally secure engagement of the flossing substrate 12 with the handles and is preferred in all modes of the device 10 herein. In the mode of the device 10 with two flossing substrates 12, this engagement additionally provides a means to define the separation distance "Z" between the parallel paths of both flossing substrates 12.

Figure 36:
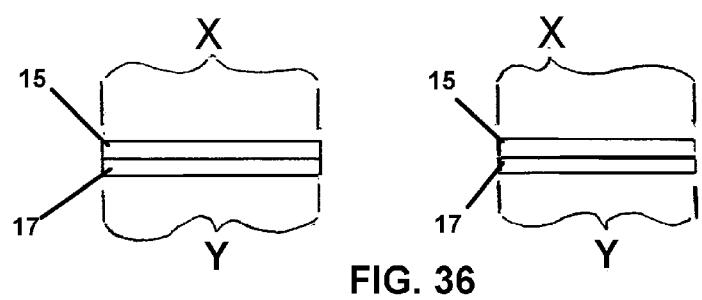
FIG. 36 shows a cross-sectional view of the device of FIG. 34 along line AA-AA.

FIG. 36 shows a cross-sectional view of the device 10 of FIG. 34 along line AA-AA which shows the first planar portion 15 is directly engaged to the second planar portion 17 of both the first handle 14 and second handle 16 in areas where the two substrates 12 are not in the sandwiched engagement therebetween.

While all of the fundamental characteristics and features of the improved flossing invention have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention. Consequently, all such modifications and variations and substitutions are included within the scope of the invention as defined by the following claims.

What is claimed:

1. A dental floss apparatus for cleaning a gap between two adjacent teeth in the surrounding mouth of a user comprising:
   a strand of flossing substrate extending a length in-between respective first ends of a respective pair of handles from respective permanent engagements of one each of two distal ends of said strand, with a respective one of said pair of handles;
   said handles having a second end opposite said first end and having opposing side edges running a length of said handle therebetween,
   an area of each said handle defined by an area between said first end, said second end and said side edges of each said handle, defining a respective handle compressive surface area configured for a compressive engagement in-between a finger and thumb of opposing hands of a user for pulling said handles in substantially opposite directions and rendering said length of said flossing substrate to an as-used position, tensioned and with said length of said flossing substrate extending along a line running in-between said respective first ends of said handles;
   a transversely centered and longitudinally centered slit positioned within each of said handles, wherein each of the longitudinal centered slit being dimensioned large enough to be capable to be penetrated by user's forefinger;
   a portion of said strand of flossing substrate overlapping the entire length of each handle in a permanent engagement thereto; and
   translation of said dental floss apparatus in said as-used position while inserted within said gap, providing a translating contact of the entire said length of said flossing substrate with surfaces of said teeth.

2. The dental floss apparatus of claim 1 wherein the portion of said strand of flossing substrate overlapping the entire length of each handle in a permanent engagement comprises:
   an extension of said substrate in a contact between two engaged sides of each respective said handle thereby positioning said substrate within said compressive engagement.

3. The dental floss apparatus of claim 2 additionally comprising:
   said handles formed of flexible material; and
   said flexible material elastically expanding in, a splayed portion of said handle compressive surface area of said handles, to a shape complimentary to that of a curved surface of one of said thumb or said finger of each respective hand of said user while said length of said flossing substrate is in said as-used position; and
   said splayed portion thereby increasing an area of surface contact of said thumb or finger with a respective said handle compressive surface area during said compressive engagement and providing a means to enhance said compressive engagement and prevent slipping.

4. The dental floss apparatus of claim 3 additionally comprising:
   said strand of flossing substrate extending between respective-engagements with each said handle in an offset position from each of said pair of handles; and said offset position being closer to one of said opposing side edges than to the other of said opposing side edges.

5. The dental floss apparatus of claim 3 additionally comprising:
at least one dissolvable component positioned adjacent respective first ends of said pair of handles in an engagement with one of said handles or with said flossing substrate.

6. The dental floss apparatus of claim 2 additionally comprising:
said strand of flossing substrate extending between respective engagements with each said handle in an offset position from each of said pair of handles; and
said offset position being closer to one of said opposing side edges than to the other of said opposing side edges.

7. The dental floss apparatus of claim 2 additionally comprising:
at least one dissolvable component positioned adjacent respective first ends of said pair of handles in an engagement with one of said handles or with said flossing substrate.

8. The dental floss apparatus of claim 1 additionally comprising:
said handles formed of flexible material; and
said flexible material elastically expanding at a splayed portion of said handle compressive surface area of said handles, to a shape complimentary to that of a curved surface of one of said thumb or said finger of each respective hand of said user while said length of said flossing substrate is in said as-used position; and
said splayed portion thereby increasing an area of surface contact of said thumb or finger with a respective said handle compressive surface area during said compressive engagement and providing a means to enhance said compressive engagement and prevent slipping.

9. The dental floss apparatus of claim 8 additionally comprising:
said strand of flossing substrate extending between respective engagements with each said handle in an offset position from each of said pair of handles; and
said offset position being closer to one of said opposing side edges than to the other of said opposing side edges.

10. The dental floss apparatus of claim 8 additionally comprising:
at least one dissolvable component positioned adjacent respective first ends of said pair of handles in an engagement with one of said handles or with said flossing substrate.

11. The dental floss apparatus of claim 1 additional comprising:
a pair of said strands of flossing substrate extending a respective said length in-between respective first ends of said respective pair of handles from the respective said permanent engagements with each said handle; said of strands of flossing substrate while tensioned in said as-used position, being spaced from each other a distance defining a void therebetween, and running substantially parallel.

12. The dental apparatus of claim 11 wherein said respective permanent engagements of each of said pair flossing substrates with each respective said handle comprise:
a portion of each said strands in said pair of flossing substrates overlapping the entire length of each handle in a permanent engagement between two engaged sides of each respective said handle thereby positioning said pair of strands of flossing substrate within said compressive engagement.

13. The dental floss apparatus of claim 12 additionally comprising:
said handles formed of flexible material; and
said flexible material elastically expanding in a splayed portion of said handle compressive surface area of said handles, to a shape complimentary to that of a curved surface of one of said thumb or said finger of each respective hand of said user positioning said length of said flossing substrate in said as-used position; and
said splayed portion thereby increasing an area of surface contact of said thumb or finger with a respective said handle compressive surface area during said compressive engagement and providing a means to enhance said compressive engagement and prevent slipping.

14. The dental floss apparatus of claim 12 additionally comprising:
at least one dissolvable component positioned adjacent respective first ends of said pair of handles in an engagement with one of said handles or with one of said pair of flossing substrates.

15. The dental floss apparatus of claim 11 additionally comprising:
at least one dissolvable component positioned adjacent respective first ends of said pair of handles in an engagement with one of said handles or with one of said pair of flossing substrates.

16. The dental floss apparatus of claim 1 additionally comprising:
said strand of flossing substrate extending between respective engagements with each said handle in an offset position from each of said pair of handles; and
said offset position being closer to one of said opposing side edges than to the other of said opposing side edges.

17. The dental floss apparatus of claim 1 additionally comprising:
at least one dissolvable component positioned adjacent respective first ends of said pair of handles in an engagement with one of said handles or with said flossing substrate.

\* \* \* \* \*